US005324750A

United States Patent [19]
Lincoln et al.

[11] Patent Number: 5,324,750
[45] Date of Patent: Jun. 28, 1994

[54] COMPOSITIONS AND METHODS FOR DRUG DELIVERY AND CHROMATOGRAPHY

[75] Inventors: Stephen F. Lincoln, Stonyfell; John H. Coates, North Adolaide; Christopher J. Easton, Bellevue Heights, all of Australia; Stephen J. Van Eyk, Ludwigshafen, Fed. Rep. of Germany; Bruce L. May, Tranmere, Australia; Paramjit Singh, Queensland, Australia; Michael L. Williams, Brompton, Australia; Martyn A. Stile, Parkside, Australia

[73] Assignee: Australia Commercial Research & Development Limited, Brisbane, Australia

[21] Appl. No.: 979,451

[22] Filed: Nov. 20, 1992

Related U.S. Application Data

[63] Continuation of Ser. No. 684,888, filed as PCT/AU89/00359, Aug. 23, 1989, abandoned.

[30] Foreign Application Priority Data

| Aug. 31, 1988 | [AU] | Australia | PJ0165 |
|---|---|---|---|
| Sep. 1, 1988 | [AU] | Australia | PJ0189 |
| Sep. 27, 1988 | [AU] | Australia | PJ0618 |
| Oct. 19, 1988 | [AU] | Australia | PJ1053 |
| Oct. 27, 1988 | [AU] | Australia | PJ1198 |
| Nov. 11, 1988 | [AU] | Australia | PJ1417 |
| Jun. 26, 1989 | [AU] | Australia | PJ4894 |
| Jun. 26, 1989 | [AU] | Australia | PJ4909 |
| Jul. 3, 1989 | [AU] | Australia | PJ5034 |
| Jul. 17, 1989 | [AU] | Australia | PJ5278 |
| Jul. 19, 1989 | [AU] | Australia | PJ5354 |
| Aug. 3, 1989 | [AU] | Australia | PJ5576 |
| Aug. 7, 1989 | [AU] | Australia | PJ5641 |
| Aug. 9, 1989 | [AU] | Australia | PJ5682 |

[51] Int. Cl.$^5$ .......... C08B 37/16; C08L 5/16; A61K 47/00; A01N 25/00
[52] U.S. Cl. .......... 514/570; 514/58; 514/557; 536/103; 560/105; 562/406; 562/494
[58] Field of Search .......... 536/103; 514/570, 58, 514/557; 560/105; 562/494

[56] References Cited

U.S. PATENT DOCUMENTS

| 3,687,982 | 8/1972 | Young | 549/270 |
|---|---|---|---|
| 4,303,787 | 12/1981 | Horikoshi et al. | 536/103 |
| 4,418,144 | 11/1983 | Okada et al. | 536/103 |
| 4,542,234 | 9/1985 | Reilly et al. | 562/443 |
| 4,959,472 | 9/1990 | Wood et al. | 544/258 |
| 4,960,762 | 10/1990 | Sellergren et al. | 514/58 |
| 5,019,563 | 5/1991 | Hunter et al. | 514/58 |
| 5,024,997 | 6/1991 | Motola et al. | 514/58 |

*Primary Examiner*—Ronald W. Griffin
*Attorney, Agent, or Firm*—Foley & Lardner

[57] ABSTRACT

Cyclodextrin derivatives and inclusion complexes having increased solubility and stability are provided. Cyclodextrin derivatives include amino and other modified cyclodextrins, and linked cyclodextrins. Inclusion complexes comprising the foregoing cyclodextrins, and processes for making the cyclodextrin derivatives are disclosed. Also disclosed are cyclodextrin derivatives comprising otherwise substituted or unsubstituted cyclodextrins covalently bonded to agents such as pharmaceuticals. The covalent bond, when broken, yields the agent in active form. Pharmaceutical compositions and methods of treating an animal host are also described, as well as chromatographic compositions and a method for separating racemic mixtures.

7 Claims, 5 Drawing Sheets

COMPOSITIONS AND METHODS FOR DRUG DELIVERY AND CHROMATOGRAPHY

This application is a continuation of application Ser. No. 07/684,888, filed as PCT/AU89/00359, Aug. 23, 1989, now abandoned.

BACKGROUND OF THE INVENTION

This invention relates to derivatives of the cyclodextrins (which are cyclic oligosaccharides), inclusion complexes comprising cyclodextrin derivatives, and to processes for preparing and using the derivatives and complexes. This invention also relates to cyclodextrin derivatives useful as synthetic intermediates, and to processes for preparing such intermediates. This invention also relates broadly to pharmaceutical, pesticidal, herbicidal, agricultural, cosmetic or personal care agent compositions comprising the cyclodextrin derivatives and inclusion complexes. This invention further relates to pharmaceutical compositions, and to processes for treating animals, including humans. This invention also relates to chromatographic compositions, and to a method for separating racemic mixtures.

Inclusion complexes are chemical species consisting of two or more associated molecules in which one of the molecules, the "host", forms or possesses a cavity into which it can admit a "guest" molecule, resulting in a stable association without formation of any covalent bonds. Secondary forces are alone responsible for maintenance of the integrity of all inclusion complexes.

Over the past twenty-five years, interest in the physical and chemical properties of inclusion complexes has grown considerably. The cyclodextrins, because they are nontoxic and are able to form complexes with numerous small organic molecules, perhaps the most important of all compounds capable of acting as host components. The three most important cyclodextrins are the $\alpha$-, $\beta$- and $\gamma$-cyclodextrins, which respectively consist of six, seven and eight $\alpha$-D-gluco-pyranosyl residues. Cyclodextrins are not perfectly cylindrical molecules, but are somewhat coneshaped, with all of the secondary hydroxyl groups situated at one end of the annulus (the larger diameter end) and all of the primary hydroxyl groups at the other, as illustrated in FIG. 1.

Each glucopyranose residue contains three hydroxyls which are of varying reactivity. The primary or C6 hydroxyl is the most reactive by virtue of its position on the C6 carbon, which is the only primary carbon. The secondary or C2 and C3 hydroxyls are less reactive because of their location on the C2 and C3 carbons, which are secondary carbons. Thus, synthetic reactions will usually involve one or more of the C6 hydroxyls unless steps are taken to proceed via the C2 and/or C3 hydroxyls.

The numbering system and structure of $\beta$-cyclodextrin are shown in FIG. 2. Viewing the secondary end of the cyclodextrin, each glucopyranosyl residue is labelled clockwise from A to F, G or H (for $\alpha$-, $\beta$- and $\gamma$-cyclodextrins, respectively). The A residue is determined by the substitution which takes priority. Thus each substituent is assigned a prefix indicating the number of the carbon to which the substituent is attached and the letter of the glucopranose residue. For example, $6^A$-o-toluenesulfonyl-$\beta$-cyclodextrin indicates that a toluenesulfonyl is attached to the oxygen on the C6 carbon of the A-glucopyranose residue.

The cavity of a cyclodextrin is relatively apolar and thus cyclodextrins will normally preferentially include apolar or hydrophobic molecules (or portions thereof) in their cavities, while excluding polar or hydrophilic molecules or portions thereof. The molecular dimensions and solubility of $\alpha$-, $\beta$-, and $\gamma$-cyclodextrin are provided in Table 1.

TABLE 1

| Physical Properties of Cyclodextrins | | | | |
|---|---|---|---|---|
| Number of D-glucosyl residues | Name | Molecular weight | Solubility in water (g/100 mL) | Cavity width (pm) |
| 6 | alpha cyclodextrin | 972 | 14.5 | 470–520 |
| 7 | beta cyclodextrin | 1135 | 1.85 | 600–640 |
| 8 | gamma cyclodextrin | 1297 | 23.2 | 750–830 |

As shown in Table 1, the space within the cyclodextrin cavity increases with the number of D-glucopyranosyl residues. Thus, as would be expected, the stability of an inclusion complex depends to a large degree on the relative sizes of the cyclodextrin cavity and the portion of the guest molecule to be included. For example, a molecule may be too large to fit within the cavity of $\alpha$-cyclodextrin, but might form a complex with the larger $\beta$-cyclodextrin. A further discussion of the molecular interaction of inclusion complexes is provided in R. J. Clarke, J. H. Coates and S. F. Lincoln, "Inclusion Complexes of the Cyclomalto-Oligosaccharides (Cyclodextrins)", *Advances in Carbohydrate Chemistry and Biochemistry*, Vol 46, pp 205–249 (1988), which is expressly incorporated herein by reference.

Cyclodextrins have been widely investigated for use in the pharmaceutical industry because of their reported ability to solubilize and stabilize drugs and to increase bioavailability. This ability has led to many scientific publications, and numerous worldwide patents and published applications relating to the use of cyclodextrins with pharmaceuticals. See, for example, U.S. Pat. No. 4,727,064 to Pitha and U.S. Pat. No. 4,707,472 to Inagaki et al., U.S. Pat. No. 4,774,329 to Friedman, and U.S. Pat. No. 4,432,802 to Harata et al., U.S. Pat. Nos. 4,518,588 and 4,274,985 to Szejtli et al., U.S. Pat. No. 4,722,815 to Shibanai, U.S. Pat. No. 4,598,070 to Ohwaki et al., and U.S. Pat. No. 4,424,209 to Tuttle, and the references cited therein.

Despite all of this research activity, the commercial use of cyclodextrins to deliver drugs has remained relatively low for a few reasons. First, while each type of cyclodextrin can form inclusion complexes by including other molecules in the annulus, for a variety of drugs in common usage the $\beta$-cyclodextrin annulus is the most appropriate size. Although $\beta$-cyclodextrin is the most readily available and least expensive cyclodextrin, it is also the lowest in solubility (1.85 g/100 ml) which substantially decreases its utility as a drug delivery system. This is especially true when the drug is itself substantially insoluble; the resulting inclusion complex generally having a solubility somewhere between the solubility of the drug and cyclodextrin. Thus, one of the main benefits of cyclodextrins, i.e., the ability to solubilize otherwise insoluble drugs, is lost when $\beta$-cyclodextrin is used to include the drug.

Another main benefit of cyclodextrins, i.e., the ability to stabilize and increase the bioavailability of drugs, stems from the ability of cyclodextrins to strongly include a drug molecule. These benefits are particularly important where (1) the drug is rendered inactive by hydrolysis in the acidic environment of the stomach, which has a pH of generally less than about 3, (2) the drug irritates the gastrointestinal lining such as, for example, non-steroidal anti-inflammatory compounds, or (3) the drug has a short half-life such that it is immediately absorbed through the lining of the small intestine, and within a few hours, is no longer present in effective serum concentrations. It is the ability of cyclodextrins to form highly stable inclusion complexes which in fact prevents the drug from being freely available to undergo hydrolysis, irritate the stomach lining or absorb too quickly into the blood stream. This ability, however, depends upon whether the molecular dimensions of the drug molecule happen to fit one of the three cyclodextrins, so that a strong intermolecular attraction exists resulting in a high stability constant.

The stability constant (or association constant), K, of cyclodextrin inclusion complexes is a measure of the proportions of free drug and free cyclodextrins in solution versus the concentration of drug-cyclodextrin inclusion complex (or included drug).

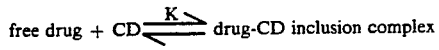

$$K = \frac{[\text{drug-cyclodextrin inclusion complex}]}{[\text{free drug}][\text{cyclodextrin}]}$$

When the stability constant is high only a small proportion of the drug is in the free state in the gastrointestinal tract. Thus only a small proportion of the drug will be exposed to hydrolysis and will be available to cause gastrointestinal irritation, and in the case of a drug of low solubility, to precipitate. However, as the drug is absorbed in the small intestine, further drug will be rapidly released in a controlled manner, from the drug-cyclodextrin inclusion complex, so that a continuous absorption of the drug by the small intestine occurs.

Obviously, when the stability constant is low the proportion of the drug free in the gastrointestinal tract will be high. This exposes a large proportion of the drug to hydrolysis. A large proportion of the drug is also available to cause irritation of the gastrointestinal tract. If the free drug is of low solubility, precipitation of solid drug will occur in the gastrointestinal tract.

While there have been some fairly high stability constants reported (e.g., up to $3.7 \times 10^4$ for some $\gamma$-cyclodextrin-steroid systems; Uekama et al., *Int. J. Pharmaceuticals*, Vol. 10 (1982) pp 1-15), most known cyclodextrin-drug inclusion complexes have stability constants only on the order of from less than about $10^3$ $M^{-1}$ up to about $10^4$ $M^{-1}$ (especially for smaller drug molecules), and it is for this reason that cyclodextrins have not gained widespread popularity. Moreover, given the wide range of molecular sizes exhibited by drug molecules, only a fraction of the drugs needing a superior delivery system will be of correct size to form an inclusion complex of high stability with one of the three naturally occurring cyclodextrin molecules.

It is apparent that high stability constants are required to ensure a high proportion of included drug molecules and thus why cyclodextrins have yet to achieve widespread commercial use. A perspective of stability constants can be gained from the following model, which follows Habon, et al., *J. Pharmazie*, Vol 39, pp 830-834 (1984) and assumes a drug solubility of $10^{-4}$M (relatively insoluble) and a 1:1 drug/CD complex solubility of $10^{-3}$M, with a total of $10^{-4}$ mole of drug/CD complex present. If one assumes a stability constant of $10^4$ $M^{-1}$ (relatively high) and a total volume of solution of 100 ml, (approximately an unfilled human stomach, e.g., before a meal), 40% of the drug would be present as undissolved (i.e., insoluble) solid drug, 10% as dissolved drug and only 50% as dissolved complex. For a stability constant of $10^4$ $M^{-1}$ and a total volume of 1000 ml (approximately a filled human stomach), 62% of the drug would be present as dissolved pure drug and only 38% as a dissolved drug/CD complex. For a stability constant of $10^2$ $M^{-1}$ and a total volume of 1000 ml, 99% of the drug would be present as dissolved pure drug and only 1% a drug/CD complex.

In attempts to overcome these problems, researchers have tried using either modified cyclodextrins, which have groups or pendant arms substituted onto the cyclodextrins, or polymeric cyclodextrins which generally comprise either randomly polymerized cyclodextrins, or cyclodextrins randomly attached to a preformed polymer backbone.

There have also been other attempts to prepare modified cyclodextrins, although the study of many such modified cyclodextrins has been confined mostly to observing interactions with dyes or other agents which are not pharmaceutical, pesticidal, herbicidal or agricultural. Moreover, the descriptions of the synthetic procedures in some instances appear insufficient to enable others of ordinary skill to reproduce the reported work.

In the case of modified cyclodextrins, those that are currently available are characterized by having some or all of their hydroxyl hydrogens replaced by methyl, ethyl, hydroxyethyl or hydroxypropyl. Such modifications lead in some cases to enhanced solubility of the cyclodextrin and its inclusion complexes formed with poorly soluble drug molecules, but do not address the problem of increasing the drug-cyclodextrin stability constants. Moreover, many of these modified cyclodextrins are the products of modifications which can be controlled only to a limited extent, and which yield a relatively inseparable mixture of mono-, di- and other randomly multisubstituted cyclodextrins. The cyclodextrin product is thus identifiable only in terms of a "degree of substitution." In the case of cyclodextrin polymers, it can also be likewise difficult to control the reaction and thus one cannot generally be certain of the product. Moreover there is also a problem with efficiency, i.e., large amounts of cyclodextrin are required to deliver only small amounts of included drug, resulting in the patient having to swallow many capsules or tablets to obtain a normal dose of a drug.

Another type of modification has been the covalent linking of two cyclodextrin molecules as reported by Fujita et al., *J. Chem. Soc., Chem. Commun.*, (1984) 1277-1278, and *Chemistry Lett.*, (1985) 11-12; Harada et al., *Polymer J.*, Vol. 12 (1980) pp 29-33; and Tabushi et al., *J. Am. Chem. Soc.*, Vol. 101 (1979) pp 1614 et seq. However, no further works has been performed to determine whether linked cyclodextrins are useful for including pharmaceuticals or other useful agents which can have intended bio-affecting activity, for example, pesticides, herbicides and agricultural products.

In a modification reported by Tabushi et al., *J. Am. Chem. Soc.*, Vol. 108 (1986) 4514-4518, $\beta$-cyclodextrin was doubly substituted with amine and carboxylic acid pendant arms. These functionalities allowed for an increased association with the amino acid, tryptophan, which was included in the cyclodextrin annulus. Again, there have been no attempts to form such associations with, for example, associable groups of pharmaceutical agents for delivering drugs into human or other host animals.

Kojima et al. reported covalently bonding the vitamin nicotinamide to a cyclodextrin. *Tetrahedron Lett.*, Vol. 21 (1980) 2721. However, the resulting cyclodextrin derivative would not have been suitable for delivery of the vitamin to a host animal because the tertiary amine bond created between the nicotinamide and the cyclodextrin, if broken, would not yield the nicotinamide in active form. Moreover, that bond would not break in a host animal under the conditions normally found, for example, the acidic conditions of the stomach.

In summary, despite the large volume of research relating to modified and unmodified cyclodextrins, there remains a long felt need for cyclodextrin derivatives and inclusion complexes which have good solubility properties and which can deliver problem drugs in a pharmacologically acceptable manner. This long felt need has been accompanied by the need for processes and intermediates by which such derivatives and complexes can be readily prepared.

It is against this background that the present invention is brought forth. While much of the foregoing discussion has dealt with the use of cyclodextrins to deliver drugs, those skilled in the art, upon reading this disclosure, will recognize many other commercial applications for this invention such as, for example, delivery systems for pesticides, herbicides, agricultural products such as feeds and fertilizers, and food additives, to name only a few.

SUMMARY OF THE INVENTION

This invention provides a new delivery system for pharmaceuticals and other agents based on the molecular encapsulation of drugs by cyclodextrin derivatives including modified and/or linked cyclodextrins. This invention also provides a new delivery system based on the covalent linking of drugs to cyclodextrins. Thus, cyclodextrin derivatives can be used to molecularly encapsulate a range of drug molecules (thereby forming high stability "inclusion complexes" or "prodrugs") such as if a quantity of the encapsulated drug is taken orally, a substantial portion of the drug molecules will remain encapsulated until they reach the small intestine. The molecules will be released as the cyclodextrin is metabolized to glucose over the ensuing 12 to 24 hours in the small intestine. Encapsulation of drugs by cyclodextrin results, for certain drugs, in improved bioavailability of the drug, substantial reduction or elimination of deleterious side effects on the stomach lining, substantial reduction or elimination of the destruction of the drug in the stomach, improved drug solubility (where this is a problem with the free drug), and improved microdispersion of the drug. This represents a substantial improvement on current drug delivery methods.

Accordingly, a first group of embodiments provides inclusion complexes comprising amino cyclodextrin derivatives in which at least one C2, C3 or C6 cyclodextrin hydroxyl is substituted with $-NH_2$. It has been discovered that such cyclodextrin derivatives are unexpectedly soluble, which is even further true of their salts. Of special interest are the monosubstituted cyclodextrins having the $-NH_2$ at the C6 position, particularly for β-cyclodextrins. A process is provided for solubilizing pharmaceuticals with the amino cyclodextrins.

Another group of embodiments provides processes for making the amino derivatives, including processes for (1) isolating the amino derivatives from mixtures which also contain powder catalysts, (2) synthesizing the amino derivatives through a cyclodextrin-guanidine intermediate, and (3) efficiently isolating monosubstituted cyclodextrins such as $6^4$-O-tosyl cyclodextrins from mixtures which also contain unsubstituted, and di- and other multisubstituted cyclodextrins.

Another embodiment provides inclusion complexes comprising at least one pharmaceutical, pesticidal, herbicidal or agricultural agent included in a broad range of cyclodextrin derivatives. Of particular importance are the amino cyclodextrin derivatives having substitutions for one or both of the amino hydrogens, diamino cyclodextrin derivatives, ester- and aminde-containing cyclodextrin derivatives, and cyclodextrin derivatives on which there is at least one associable portion that associates with at least one associable portion of an included pharmaceutical, pesticidal, herbicidal or agricultural agent. Related embodiments provide processes for preparing ester- and amide-containing cyclodextrin derivatives, which derivatives are useful in forming inclusion complexes or as synthetic intermediates. A process is also provided for solubilizing pharmaceuticals with such modified cyclodextrins.

Other embodiments provide two or more cyclodextrins covalently bonded to each other by at least one linking group, and inclusion complexes comprising the linked cyclodextrins, as well as processes for preparing the linked cyclodextrins.

In another embodiment, a cyclodextrin derivative is formed by covalently bonding a substituted or unsubstituted cyclodextrin to a pharmaceutical, pesticidal, herbicidal or agricultural agent, such that the covalent bond, when broken, yields the agent an active form. In other embodiments, the agent is covalently bound in a similar manner to linked and polymeric cyclodextrins. Other embodiments provide processes for making such derivatives. Another embodiment provides a process for delivering a drug to a host animal.

Other embodiments provide compositions comprising at least two different inclusion complexes, at least two different cyclodextrin derivatives, or at least one inclusion complex and at least one cyclodextrin derivative selected from the previously described inclusion complexes and derivatives. In a preferred embodiment, the combination of cyclodextrin derivatives and inclusion complexes are selected to effect an improved delivery of a pharmaceutical agent.

Other embodiments provide pharmaceutical compositions comprising the cyclodextrin derivatives and inclusion complexes of the invention in combination with pharmaceutically acceptable carriers. Methods for treating a host animal, including a human, comprising administering therapeutically effective amounts of the pharmaceutical compositions of this invention are also provided.

Yet other embodiments provide processes for "tailoring" cyclodextrin derivatives in order to form drug delivery systems.

Embodiments of this invention also provide chromatographic compositions, and a process for separating the enantiomers of a racemic mixture.

Accordingly, it is an object of this invention to provide inclusion complexes which have suitable solubility and stability properties, particularly when pharmaceutical agents are included.

It is another object of this invention to provide cyclodextrin derivatives which can be used to form inclusion complexes with pharmaceutical or other useful agents.

It is another object of this invention to provide cyclodextrin derivatives which comprise a pharmaceutical, pesticidal, herbicidal, agricultural, cosmetic or personal care agent covalently bonded to a substituted or unsubstituted cyclodextrins, wherein the covalent bond, when broken will yield the agent in active form.

Another object of this invention is to provide linked cyclodextrin derivatives comprising two or more cyclodextrins linked together, and inclusion complexes comprising linked cyclodextrins with pharmaceuticals or other useful agents.

Other objects are to provide synthetic intermediate and processes for making the cyclodextrin derivative and inclusion complexes of this invention.

Other objects are to provide pharmaceutical compositions comprising the cyclodextrin derivatives and inclusion complexes, and methods for treating animals using such compositions.

Other objects are to provide a process for separating a racemic mixture, and chromatographic compositions useful for various separations.

Additional objects and advantages of the invention will be set forth in part in the description that follows, and in part will be obvious from the description, or may be learned by practice of the invention. The objects and the advantages of this invention may be realized and obtained by means of the compositions of matter and processes particularly pointed out in the appended claims.

DESCRIPTION OF THE PREFERRED EMBODIMENTS

I. Definitions

Figure 1:
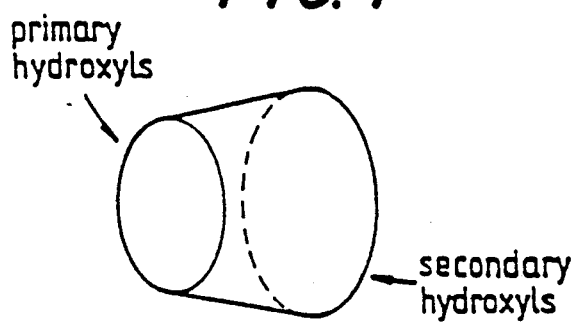
FIG. 1 illustrates the relative positions of the primary and the secondary hydroxyls of a cyclodextrin molecule.
Figure 2:
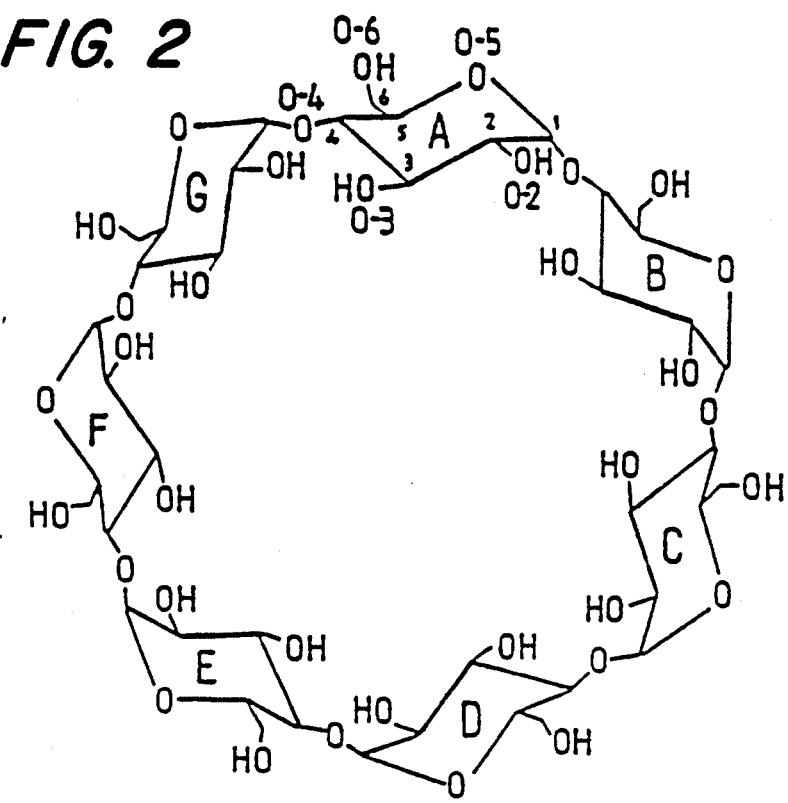
FIG. 2 illustrates the numbering system and the structure of β-cyclodextrin.

The following definitions are provided for some basic terms that are used throughout this specification.

Cyclodextrin—refers to α-, β- or γ-cyclodextrins, which are those that are generally available. It will be appreciated, however, that if other cyclodextrins are discovered or become available in sufficient commercial quantities, such cyclodextrins shall also be encompassed by this invention.

Cyclodextrin Derivative—refers to a cyclodextrin-containing compound in which one or more atoms or groups of atoms are substituted for a C2, C3 or C6 hydroxyl or hydroxyl hydrogen, i.e. "modified cyclodextrins." The term cyclodextrin derivative also encompasses "linked cyclodextrins" where two or more cyclodextrins are linked together, and compounds where a useful agent such as pharmaceutical is covalently bonded to a cyclodextrin, such that the covalent bond, when broken will yield the agent in active form. This term also includes any salt or hydrate which can be formed from the cyclodextrin derivative.

Modified Cyclodextrin—refers to a species of cyclodextrin derivatives that contains one or more atoms or groups of atoms substituted for a C2, C3 or C6 hydroxyl or hydroxyl hydrogen. The term modified cyclodextrin will not be meant to include compounds where two or more cyclodextrins are linked together, or compounds where a useful agent such as a pharmaceutical is covalently bound to a cyclodextrin. This term also includes any salt or hydrate which can be formed from the modified cyclodextrin.

Linked Cyclodextrins—refers to two or more cyclodextrins linked together by one or more bridging groups. The bridging groups can link a C2, C3 or C6 position of one cyclodextrin to any one of the C2, C3, or C6 positions of the other cyclodextrin. This term includes any salt or hydrate which can be formed from the linked cyclodextrins.

Prodrug—refers to a cyclodextrin derivative in which a pharmaceutical agent is covalently bonded to a substituted or unsubstituted cyclodextrin or to two or more linked cyclodextrins such that the covalent bond, when broken, yields the agent in active form. The product formed by this reaction comprises the residue of the pharmaceutical linked to a cyclodextrin, or to a pendant arm substituted thereon, through a linking group that is formed by the reaction of a functional group on the pharmaceutical agent with a functional group on the cyclodextrin or pendant arm. Thus, the residue of a pharmaceutical agent can be covalently bonded to the cyclodextrin through a linking group that is substituted for a C2, C3 or C6 hydroxyl or hydroxyl hydrogen, or it can be covalently bonded via a pendant arm that is substituted to a C2, C3 or C6 position. This term also includes any salt or hydrate which can be formed from the prodrug.

Cyclodextrin Inclusion-Association Complex—refers to an inclusion complex in which there are one or more associable groups or portions of a group located on a substituent that is substituted at a C2, C3 or C6 position of a cyclodextrin, which groups or portions form an association with one or more associable groups or portions of a guest atom or molecule. The associable portions can include polar or charged groups or portions, or groups or portions capable of hydrogen bonding. This term also includes any salt or hydrate which can be formed from the inclusion-association complex.

Cyclodextrin Inclusion Salt—refers to an inclusion-association complex in which the associable group or portion of the cyclodextrin substituent carries a net positive or negative charge which causes it to associate with an oppositely charged group or portion of a guest atom or molecule. This term also includes any other salt or a hydrate which can be formed from the cyclodextrin inclusion salt.

Pharmaceutical Agent—refers to compounds or their salts or hydrates which have a pharmaceutically recognized use. It will be appreciated that the term is not intended to cover compounds which have some type of bio-affecting activity, but which are not recognized as pharmaceutical agents by the medical community or drug regulatory agencies. For example, a dye is not considered to be a pharmaceutical agent, even though it might possess some type of bio-affecting activity. Similarly, the term "pharmaceutical agent" does not include unreacted reactants, other products, or solvents (including water) that are present in the reaction mixture when synthesizing cyclodextrin derivatives or which are present when forming inclusion complexes.

Pesticidal, Herbicidal, Agricultural, Cosmetic or Personal Care Agent—refer to compounds or their salts or hydrates which have a generally recognized use in the fields. For the purpose of this invention, a dye is not considered to be such as agent. Similarly, these terms do not include unreacted reactants, other products, or solvents (including water) that are present in the reaction mixture when synthesizing cyclodextrin derivatives or which are present when forming the inclusion complexes.

A Useful Agent—includes pharmaceutical, pesticidal, herbicidal, agricultural, cosmetic or personal care agents or salts or hydrates thereof as defined above.

Solubility—refers to solution in water or other aqueous-based media.

II. The Cyclodextrin Derivatives and Inclusion Complexes

By now it will be apparent that this invention comprises several different embodiments of cyclodextrin derivatives and inclusion complexes. In the discussion which follows, the structurally simpler embodiments are explained, and then building upon that discussion the structurally more complex cyclodextrin derivatives and inclusion complexes of this invention are discussed. A detailed discussion of the processes for preparing the cyclodextrin derivatives, inclusion complexes, and intermediates of this invention is provided in Section IV and the Examples which follow Section IV.

A. Amino Cyclodextrins

Figure 3A:
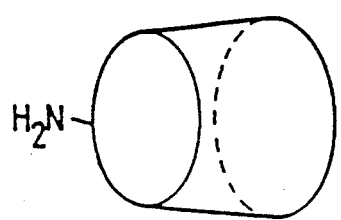
FIGS. 3A and 3B each illustrate amino cyclodextrins in accordance with this invention.
Figure 3B:
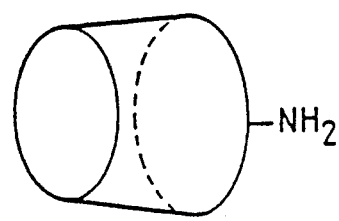

A first embodiment of this invention comprises an inclusion complex comprising a pharmaceutical, pesticidal, herbicidal, agricultural, cosmetic or personal care agent included in a cyclodextrin having one or more substitutions, wherein at least one C2, C3 or C6 hydroxyl is substituted with $-NH^2$. Illustrations of primary and secondary monosubstituted amino cyclodextrins are provided in FIGS. 3A and B.

Surprisingly, it has been discovered that such amino cyclodextrins have unexpected solubility when compared to the corresponding unsubstituted cyclodextrin. For example, whereas the solubility of unsubstituted $\beta$-cyclodextrin is only about 1.85 g/100 ml, the solubility of $6^4$-amino-$6^4$-deoxy-$\beta$-cyclodextrin is about 4.8 g/100 ml, and the hydrochloride salt has a solubility of greater than about 20 g/100 ml. Preparation of other salts such as the halide, carboxylate, carbonate, bicarbonate, sulfate and bisulfate, etc. will be well within the ordinary skill of the art. A general rule for determining the solubility of a cyclodextrin inclusion complex is that the complex will have a solubility about half-way between the solubilities of the cyclodextrin and the agent that is included. Hence, the inclusion complexes formed by the amino cyclodextrins and their salts and hydrates will also exhibit unexpected solubility.

The amino cyclodextrins perform three roles in this invention. First, they are useful intermediates in the synthesis of other cyclodextrin derivatives. Second, they are useful in forming inclusion complexes which will likewise exhibit enhanced solubilities. This will be particularly helpful in cases where the $\beta$-cyclodextrin cavity provides the best molecular fit for a guest molecule, but where the inclusion complex with the unsubstituted $\beta$-cyclodextrin does not possess the desired solubility properties. Third, as discussed more fully below, they can form inclusion salts with guests that contain a negatively charged group or portion. In cases where greater solubility is desired, it may be preferred to prepare the salt forms of the amino cyclodextrins and the resulting inclusion complexes.

B. Other Modified Cyclodextrins

In another embodiment, inclusion complexes are provided, in which at least one pharmaceutical, pesticidal, herbicidal, agricultural, cosmetic or personal care agent is included in a modified cyclodextrin. These modified cyclodextrins comprise a cyclodextrin having at least one substitution wherein a C2, C3 or C6 hydroxyl is substituted with a group selected from $-XR^1$, $-YR^2R^3$, $-SiR^4R^5R^6$, and $-R^7$, wherein X can represent

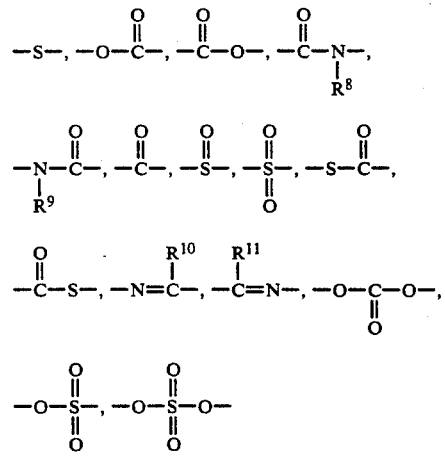

Y can represent

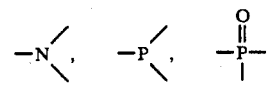

and wherein $R^1$ to $R^{11}$ can each represent the same or different groups selected from hydrogen, alkyl, alkenyl, alkynyl, cycloalkyl, cycloalkenyl, cycloalkynyl, aryl, heteroaryl, heterocyclyl, and wherein any two or three groups bonded to the same substituent can be taken together to represent a single group multiply bonded to said same substituent, and wherein $R^1$ to $R^{11}$ may be further substituted by at least one $-XR^1$, $-YR^{12}R^3$, $-SiR^5R^6$, $-R^7$, hydrogen and $OR^{12}$, wherein $R^{12}$ is as defined for $R^1$ to $R^{11}$.

Figure 4A:
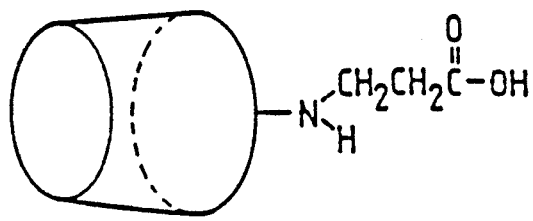
FIGS. 4A and 4B each illustrate substituted amino cyclodextrins in accordance with this invention.
Figure 4B:
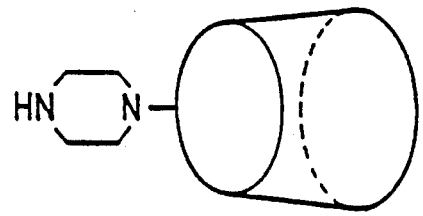

Of the above recited inclusion complexes, several groups are preferred. One such group is the substituted amino cyclodextrins, i.e., cyclodextrins wherein at least one substitution for said C2, C3 or C6 hydroxyl is of the formula $-YR^2R^3$, wherein Y is N, and $R^3$ are as previously defined, but are not both hydrogen. Also of particular interest are the inclusion complexes wherein $R^2$ is hydrogen and $R^3$ represents amino, hydroxyl or carboxyl substituted alkyl, cycloalkyl, or aryl, or wherein $R^2$ and $R^3$ are taken together to represent a hetero substituted multiply bonded alkyl group. As with the amino cyclodextrins previously described, the substituted amino cyclodextrins, their salts and hydrates, and inclusion complexes therefrom will likewise possess unexpected solubility. Examples of substituted amino cyclodextrins are provided in FIGS. 4A and B.

Figure 5:
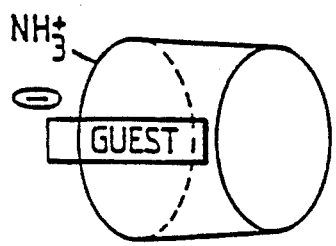
FIG. 5 illustrates a cyclodextrin inclusion salt in accordance with this invention.

Each of the above modified cyclodextrins will form unexpectedly soluble inclusion complexes, and at the same time may provide increased solubility constants by virtue of the amino, hydroxyl or carboxyl substituents, which can associate with portions of a guest molecule. In a neutral aqueous solution, the amino substituent protonates to become a positively charged $-NR_3^+$, and the carboxyl yields a proton to become a negatively charged $-COO^-$ group. Either of these groups are thus able to associate with any oppositely charged groups or portions of a guest molecule, provided the associable portions of the substituted cyclodextrin guest are in sufficient proximity, once the apolar or hydrophobic portion of the guest includes within the cyclodextrin cavity. In a similar manner, a hydroxyl is able to associate via hydrogen bonding with associable groups in the guest. One example of an inclusion salt for a negatively charged guest is illustrated in FIG. 5.

In other preferred species of the above-described inclusion complexes, the cyclodextrin derivative is substituted with $-XR^1$, which represents either

Figure 6:
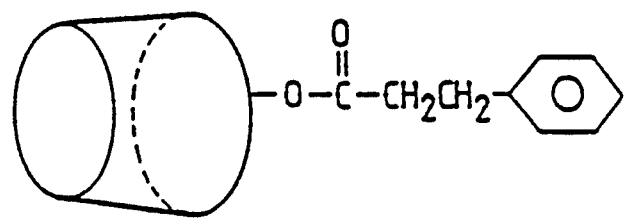
FIG. 6 illustrates a modified cyclodextrin which contains a pendant arm connected to the cyclodextrin by an ester linkage.

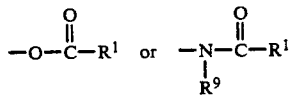

wherein $R^1$ and $R^4$ are as previously defined. The ester and amide substitutions are of particular interest because they represent other linking groups useful for attaching pendant arms onto a cyclodextrin. Moreover, such links can be used to create a pendant arms which can contain associable portions capable of forming inclusion-association complexes. A modified cyclodextrin is illustrated in FIG. 6.

C. Linked Cyclodextrins

Figure 7A:
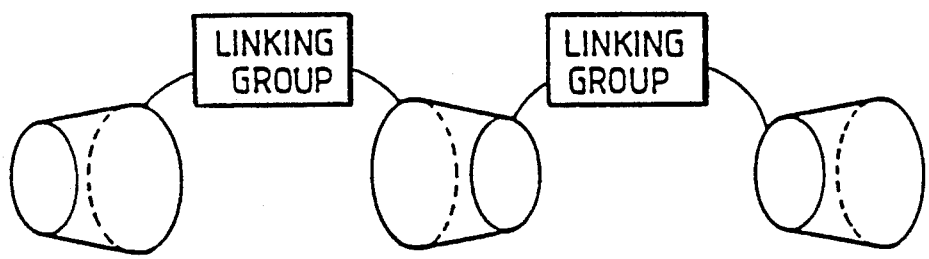
FIGS. 7A and 7B each illustrate linked cyclodextrins.
Figure 7B:
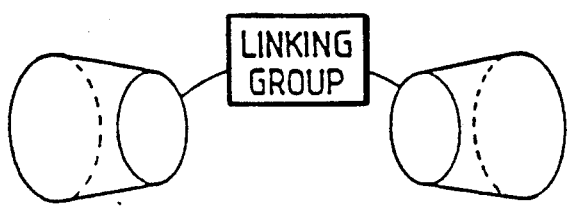

In another preferred embodiment of this invention, a cyclodextrin derivative is provided which comprises at least two otherwise substituted or unsubstituted cyclodextrins covalently bonded to each other by at least one linking group. The at least one linking group links a first cyclodextrin at a C2, C3 or C6 position to a second cyclodextrin at a C2, C3, or C6 position. When there are only two cyclodextrins which are not otherwise substituted and are linked by only one linking group, that linking group is other than a disulfide that links the two cyclodextrins at the C6 positions of each cyclodextrin. Illustrations of such linked cyclodextrins are provided in FIGS. 7A and 8.

These linked cyclodextrins can be used to prepare inclusion complexes having stability. Because inclusion complexes comprising the linked cyclodextrins possess greater stability constants, the free concentration of drug molecules in the stomach will be much smaller, and consequently, there will be less interaction of the drug with the stomach lining, and less interaction of the stomach acid with the drug. While the cyclodextrins may be linked by any covalent linking, they are preferably linked by at least one linking group of the formula:

$$-X-R^1-Y-,$$

or $$-R^2-$$

wherein X and Y can be the same or different, and represents

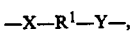

Figure 8A:
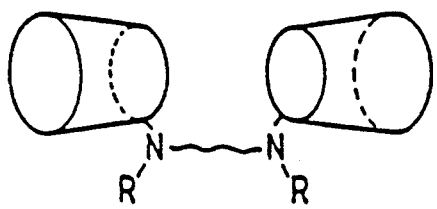
FIGS. 8A, 8B, 8C and 8D respectively illustrate diamine, diamide, diester, and diether linked cyclodextrins.
Figure 8B:
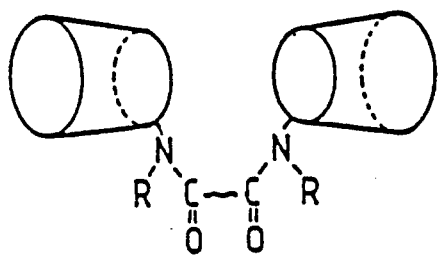
Figure 8C:
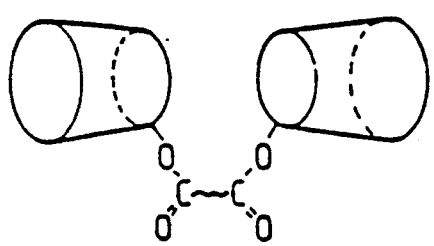
Figure 8D:
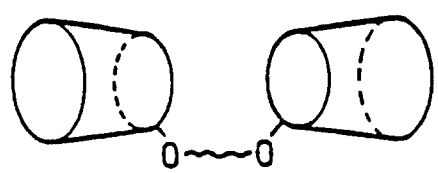

where $R^1$ to $R^5$ can each represent the same or different groups selected from substituted and unsubstituted: alkyl, alkenyl, alkynyl, cycloalkyl, cycloalkenyl, cycloalkynyl, aryl, heteroaryl, heterocyclyl, and wherein $R^3$ to $R^5$ can also be hydrogen. Linked cyclodextrins in accordance with this embodiment are illustrated in FIGS. 8A and B.

In another preferred embodiment, $-X-R^1-Y-$ is selected from groups of the formula:

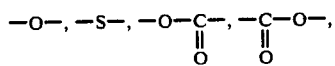

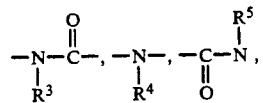

wherein
Z is $-S-$, $-O-$, or $-NH-$, and
$R^6$ to $R^9$ represent alkyl, alkenyl, or aryl.

Linked cyclodextrins are useful for preparing inclusion complexes of particularly high stability, especially where a guest molecule possesses two or more apolar or hydrophobic regions. Thus, each cyclodextrin of the linked cyclodextrins would be capable of including one of the apolar or hydrophobic reagents, thereby rendering the complex more soluble and more stable. The cyclodextrins are preferably linked by diamines, diamides, diesters or diethers which are bonded to the cyclodextrins at the C2, C3 or C6 positions. However, the linking group may also be "mixed". For example, the linking group can comprise an amine function at one end bonded at the C2 position, and an ester function at the other end bonded at a C6 position, and combinations of similar functional groups including, but not limited, to those shown above.

The length of the linking group may be varied by increasing the number of units in the chain to accommodate drug molecules of different sizes. Preferably, the linkage is stable under acidic conditions. Acid stability is determined (using spectroscopic and chromotographic methods) by measuring the rate at which the linkage break down in 0.1M hydrochloric acid. Each linkage will be characterized by its own unique half-life (the time taken for half the linkages to break down in a sample of given cyclodextrin). The half-life of diamine and diamide linkages is significantly greater than that of the diester linkages. Acid-stable linked cyclodextrins can pass through the stomach intact, but in the small intestine are rapidly broken down to glucose and the linkage components, thereby releasing the included drug. Obviously, glucose is not harmful, and the linkage components can be designed to also be harmless.

Another embodiment provides cyclodextrin derivatives in which two or more cyclodextrins are linked to form a cyclodextrin derivative of the formula:

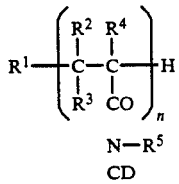

wherein CD represents a cyclodextrin substituted at least one of the C2, C3 or C6 positions, and wherein n is at least 2, and $R^1$ and $R^5$ can represent the same or different groups selected from hydrogen and substituted and unsubstituted: alkyl, alkenyl, alkynyl, cycloalkyl, cycloalkenyl, cycloalkynyl, aryl, heteroaryl, heterocyclyl; and wherein $R^1$ to $R^5$ may be further substituted with groups as defined by $R^1$ to $R^5$ or further functional groups. Preferably, the cyclodextrin derivative comprises from 3 to 5 linked cyclodextrins, and is substantially linear.

D. Cyclodextrin Derivatives Having a Covalently Bonded Agent (e.g., Prodrugs)

Figure 9A:
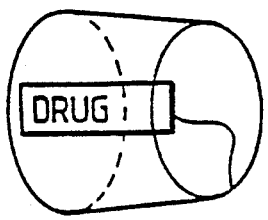
FIGS. 9A and 9B each illustrate cyclodextrin derivatives having a covalently bonded agent in accordance with this invention.
Figure 9B:
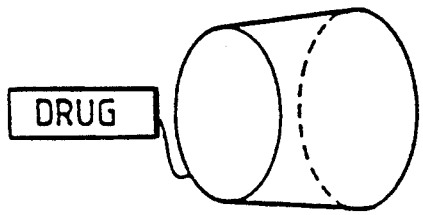

Another preferred embodiment there is provided a cyclodextrin derivative formed by covalently bonding an otherwise substituted or unsubstituted linked cyclodextrin, or two or more otherwise substituted or unsubstituted linked cyclodextrins, to a pharmaceutical, pesticidal, herbicidal or agricultural, cosmetic or personal care agent, wherein the covalent bond, when broken, will yield the agent in active form. Examples of such a cyclodextrin derivative are shown in FIGS. 9A and B.

In a preferred embodiment, the agent is reacted with a modified cyclodextrin or with linked cyclodextrins which are substituted at a C2, C3 or C6 position with a group selected from $-XR^1$, $-YR^2R^3$, $-SiR^4R^5R^6$, and $-R^7$, and wherein X represents

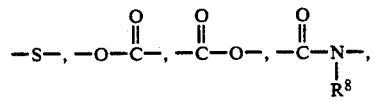

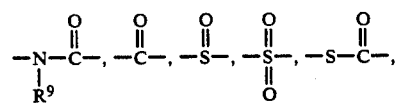

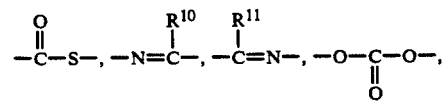

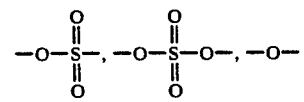

Y represents

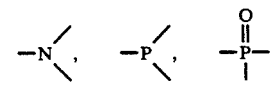

wherein $R^1$ to $R^{11}$ can represent the same or different groups selected from hydrogen, substituted and unsubstituted: alkyl, alkenyl, alkynyl, cycloalkyl, cycloalkenyl, cycloalkynyl, aryl, heteroaryl, heterocyclyl; and wherein any two or three groups bonded to the same substituent can be taken together to represent a single group multiply bonded to the same substituent, and wherein $R^1$ to $R^{11}$ may be further substituted by at least one $-XR^1$, $-YR^2R^3$, $-SiR^4R^5R^6$, $-R^7$, or halogen.

Figure 10A:
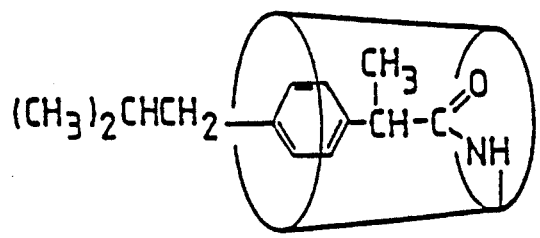
FIGS. 10A and 10B respectively illustrate prodrugs in accordance with this invention comprising Ibuprofen linked to a cyclodextrin through an ester and amide.
Figure 10B:
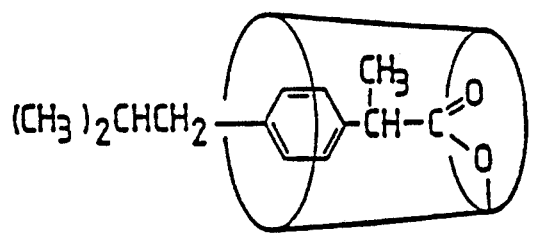

In a particularly preferred embodiment, the agent that is covalently bonded to the substituted or unsubstituted cyclodextrin is a pharmaceutical agent. In this instance, the cyclodextrin derivative is referred to as a "prodrug." In another preferred embodiment, the covalent bond is such that it is broken down by the normally occurring internal activity of a host animal such as a human. For example, a bond that is susceptible to acid hydrolysis such as that in an ester or amide, would thus be susceptible to being broken in the acidic environment of the stomach. Alternatively, the bond could be susceptible to being broken by other normally occurring internal conditions in the stomach or intestine of a host. Illustrations of prodrugs formed by covalently bonding Ibuprofen to a cyclodextrin through creation of amide and ester linking groups are shown in FIGS. 10A and B, respectively.

Because an ester is normally the product of a reaction between a carboxylic acid and an alcohol, and an amide is normally produced by reacting a carboxylic acid and an amine, preparation of prodrugs can present an advantageous delivery system when the pharmaceutical agent contains a functional group that is a carboxyl, an amino, or a hydroxyl. However, prodrugs can also be found where the pharmaceutical agent contains a thiyl or a carbonyl group (e.g., thiols, aldehydes and ketones).

Pharmaceutical agents which are carboxylic acids or which contain a carboxyl group include melphalan, chlorambucil, furosemide, piromidic acid, biphenylylacetic acid, indomethacin, captopril, amphotericin B, β-lactam, antibiotics, prostaglandins, and non-steroidal anti-inflammatory drugs such as tolmetin, naproxen, amoxicillin, ketoprofen, indomethacin, fenoprofen, diclofenac, piroxicam, pirprofen, Ibuprofen, flurbiprofen, mefenamic acid, sulindac and diflunisal.

Pharmaceutical agents which are amines or contain an amino group include bendrofluazide, melphalan, furosemide, diclofenac, cardizem, tamoxifen, sulfamethoxazole, amoxicillin, cinnarizine, vinpocetine, amphotericin B, pirporfen, bencyclane, tiamulin and carboplatin.

Pharmaceutical agents which are alcohols or phenols, or which contain an hydroxyl group include propanolol, chlorobutanol, amphotericin B, hydrocortisone, dicumarol, tiamulin, beclomethasone, prednisolone, testosterone, piroxicam, diflunisal, and prostaglandins.

The structures for these and other compounds are provided in Australian Provisional Patent Application Nos. PJ 0165, PJ 0189, PJ 0618, PJ 1053, PJ 1198, PJ 1417, PJ 4909, PJ 4894, PJ 5034, PH 5278 and PJ 5354, the disclosures of which are expressly incorporated herein by reference.

The ester and amide linking groups are preferred because they undergo hydrolysis. Conveniently, all things being generally equal, the ester will undergo hydrolysis more quickly than an amide. As discussed more fully below, these properties facilitate the design of prodrugs which will hydrolyze at a controlled rate. Thus, a prodrug may take the form of a cyclodextrin derivative which has at least one C2, C3 or C6 hydroxyl substituted with a group of the formula:

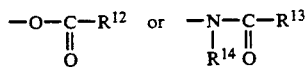

wherein $R^{12}$ and $R^{13}$ are substituents which will provide a pharmaceutically active agent upon hydrolysis of the cyclodextrin derivative, and wherein R14 is defined a prodrug in which the residue of a pharmaceutical agent is covalently linked to an otherwise substituted or unsubstituted cyclodextrin through a pendant arm. Thus, if a pharmaceutical contains a carboxyl group, the prodrug can take the form of a cyclodextrin derivative which has at least one C2, C3 or C6 hydroxyl substituted with a group of the formula:

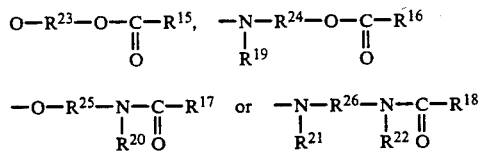

wherein $R^{15}$ to $R^{18}$ are as previously defined for $R^{12}$ and $R^{13}$, $R^{19}$ to $R^{22}$ are as previously defined for $R^1$ to $R^{11}$, and $R^{23}$ to $R^{26}$ are as previously defined for $R^1$ to $R^{11}$, except $R^{23}$ to $R^{24}$ cannot be hydrogen.

As discussed fully in Section IV, prodrugs which comprise a drug residue linked to a cyclodextrin via a pendant arm can be formed by two methods. In the first method, a pharmaceutical agent is covalently bonded to an already existing pendant arm that is substituted on a cyclodextrin. In the second method, the pendant arm is first attached to the drug by reacting a first functional group on the pendant arm with a functional group on the drug. A second functional group on the pendant arm is then reacted with a functional group on the cyclodextrin to covalently bond the pendant arm to the cyclodextrin. While both syntheses effectively result in the covalent bonding of a pharmaceutical agent to a cyclodextrin via a pendant arm, the latter synthesis can be preferred in certain circumstances.

Figure 11:
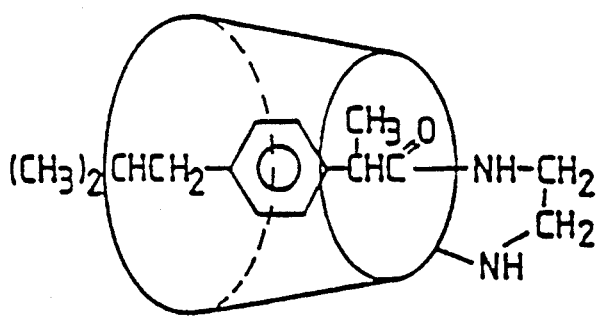
FIG. 11 illustrate a prodrug in which the residue of a pharmaceutical agent is linked to a cyclodextrin via a pendant arm.

If the pharmaceutical agent contains an amino or an hydroxyl group, the prodrug can take the form of a cyclodextrin derivative which has at least one C2, C3 or C6 hydroxyl substituted with a group of the formula:

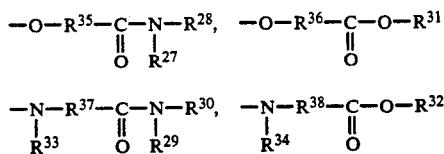

wherein $R^{27}$ to $R^{32}$ are substituents which will provide a pharmaceutically active agent upon hydrolysis of the cyclodextrin derivative, and wherein in $R^{33}$ and $R^{34}$ are as previously defined for $R^1$ to $R^{11}$, and $R^{35}$ to $R^{38}$ are as previously defined for $R^1$ to $R^{11}$, except that $R^{35}$ to $R^{38}$ cannot be hydrogen. Prodrugs in which the residue of a pharmaceutical agent is linked to a cyclodextrin via a pendant arm as defined above are illustrated in FIG. 11.

Those having ordinary skill in this art will quickly realize that there are many variations of the embodiment in which the residue of a pharmaceutical agent is linked to a cyclodextrin via a pendant arm. Moreover, by routine experimentation, one can vary the length of the pendant arm and the substituents thereon to further effect a controlled rate of hydrolysis.

For example, an amino group incorporated in a pendant arm will facilitate the release of a pharmaceutical agent from a prodrug by acting as a base in a concerted-base hydrolysis of an ester or amide linkage bonding the cyclodextrin to a pharmaceutical agent residue. The distance between the amino group and the ester or amide linkage will affect the rate of hydrolysis.

As illustrated above in FIGS. 9A and B, the residue of the pharmaceutical agent can either be included (or partially included) in the cyclodextrin annulus, or it can be outside of the annulus. An equilibrium condition between two such states is also possible. In cases where the residue is included in the annulus, the prodrug can provide a drug delivery system of particularly enhanced stability because the covalent bonds, when broken, can yield an inclusion complex in which the active pharmaceutical agent is included in the cyclodextrin annulus. Of course, the same result can occur if the drug residue is not included because once the covalent bond is broken, the active pharmaceutical agent will be free to form an inclusion complex in solution. Further, in cases where the linking group is, for example, an amide, when broken it will yield a positively charged amino group and a negatively charged carboxyl group, which are then free to associate thereby resulting in an inclusion-association complex. This inclusion-association complex, in which the association is between oppositely charged groups or portions is termed an "inclusion salt" and can provide an inclusion complex with enhanced stability.

E. Formation of Inclusion Complexes

If a solution of a cyclodextrin in water, DMF or other suitable solvent is added to a solution of an appropriate drug dissolved in the same solvent, an inclusion complex may be formed. Removal of the solvent by evaporation under reduced pressure allows recovery of the inclusion compound in the pure form.

Several different types of inclusion complexes can be formed in accordance with this invention; the complex formed being dependant upon the particular cyclodextrin derivative and guest used. FIGS. 12A to G illustrate the common types which will occur, i.e., (A) one host - one guest; (B) and (E) two hosts - one guest; (C) one host - two guests; (D), (G) and (F) and two hosts - two guests. The fact that the included species is shown as a rectangular does not imply that the included species has any particular geometry. Neither is there any implication that the included species enters from a particular end of the annulus. The "X" bonded to the cyclodextrin can represent any modification in accordance with this invention.

Figure 12A:
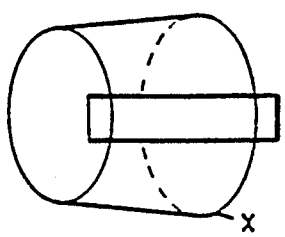
FIGS. 12A, 12B, 12C, 12D, 12E, 12F and 12G each illustrate a different one of the seven common types of inclusion comprises which can occur in accordance with this invention.
Figure 12B:
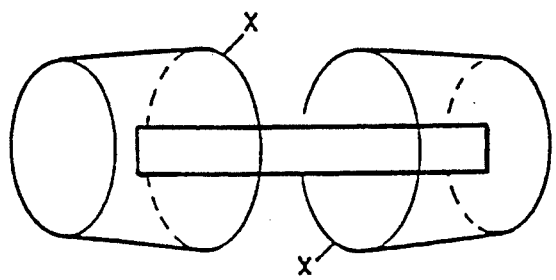

FIG. 12A illustrates a typical one host - one guest inclusion complex in which a modified cyclodextrin includes an apolar or hydrophobic portion of a guest. In FIG. 12B, a two hosts - one guest complex is illustrated, in which the guest has two apolar or hydrophobic regions, each of which is included by a modified cyclodextrin. This will be a more common occurrence in larger molecules which have multiple apolar or hydrophobic regions.

Figure 12C:
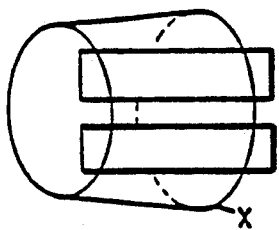
Figure 12D:
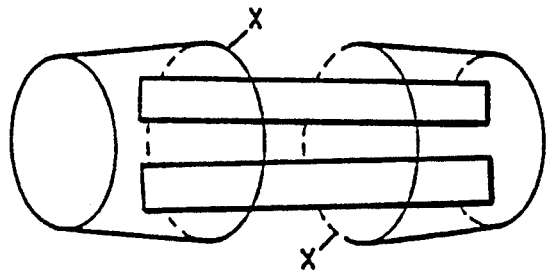

FIG. 12C illustrates a one host - two guests complex in which a cyclodextrin includes two guest molecules simultaneously. It has been found that $\beta$- and $\gamma$-cyclodextrin are able to include two guest molecules due to their larger cavity sizes. FIG. 12D illustrates a two host- two guest complex in which two modified cyclodextrins include two guests, each guest possessing two apolar or hydrophobic regions.

Figure 12E:
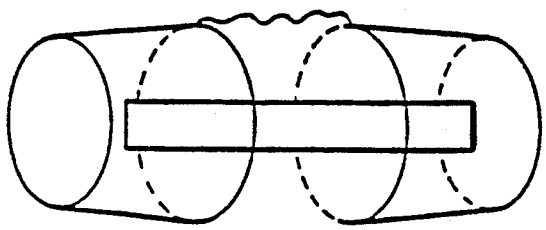
Figure 12G:
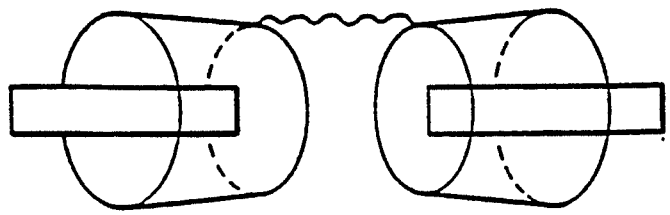
Figure 12F:
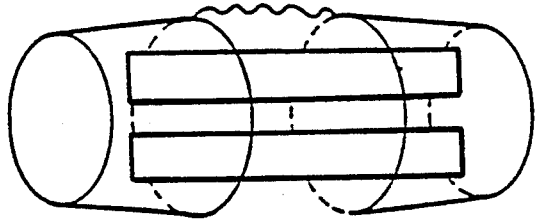

FIGS. 12E, 12F and 12G illustrate inclusion complexes which can be formed using the linked cyclodextrins of this invention. In FIG. 12E, the linked cyclodextrins are including two hydrophobic portions of the same molecule. This might be more common for relatively larger molecules which contain multiple aromatic portions. It is expected that within a linkage of appropriate length the stability constant of the inclusion complex shown in FIG. 12E will be greater than that for the complex shown in FIG. 12B. Similarly, provided the linkage is of appropriate length, the inclusion complex illustrated in FIG. 12F, in which linked cyclodextrins include two molecules, is expected to be more stable than that shown in FIG. 12D where the cyclodextrins are not linked. FIG. 12G illustrates a linked cyclodextrins including complex in which two guests are included, one in each linked cyclodextrin.

A thorough discussion of various inclusion complexes can be found in the previously mentioned publication by R. J. Clarke, J. H. Coates and S. F. Lincoln, "Inclusion Complex of the Cyclomalto-Oligosaccharides (Cyclodextrins)", *Advances in Carbohydrate Chemistry and Biochemistry*, Vol. 46, pp. 205-249 (1988).

In summary, several cyclodextrin derivatives and inclusion complexes have been provided which are useful for forming inclusion complexes with pharmaceutical, pesticidal, herbicidal, agricultural, cosmetic or personal care agents. Further provided are cyclodextrins such as prodrugs which are also useful for the delivery of pharmaceuticals and the other recited agents for their intended use.

III. Compositions and Methods of Use

This invention encompasses many different uses for the foregoing inclusion complexes and cyclodextrin derivatives. However, it will be readily apparent that such complexes or derivatives are particularly useful for drug delivery. Accordingly, other embodiments of this invention are pharmaceutical compositions comprising one of the foregoing inclusion complexes or cyclodextrin derivatives in combination with a pharmaceutical agent and a pharmaceutically acceptable carrier.

To prepare the pharmaceutical compositions of the present invention, the inclusion complexes and cyclodextrin derivatives of this invention may be combined, if desired, with pharmaceutically acceptable excipients and adjuvants. The latter may take a variety of forms depending on the form of preparation desired for administration. The pharmaceutical compositions of the present invention are desirable in unitary dosage form suitable for administering orally, rectally or by parenteral injection, the oral route of administration being preferred.

As examples of compositions in oral dosage form, there may be mentioned oral liquid preparations such as suspensions, syrups, elixirs and solutions; or powders, pills, capsules and tablets; as examples of parental compositions there may be mentioned injectable solutions and as examples of rectally applicable compositions, suppositories. Because of their ease of administration, tablets and capsules represent the most advantageous oral dosage unit form. In case of compositions in oral dosage form, the aformentioned adjuvants may take a wide variety of forms. For oral liquid preparations they comprise, for example, water, glycols, oils, alcohols and the like, whereas for solid preparations starches, sugars, kaolin, lubricants, binders, thickners, disintegrating agents and the like are most conveniently employed. For parenteral compositions said adjuvants comprise sterile water, saline solution, glucose solution or a mixture of saline and glucose solution. It will be well within ordinary skills to design and prepare the pharmaceutical compositions of this invention for such administration.

As previously discussed, the inclusion complexes, and more so the prodrugs, can be designed to effect different and controlled rates of drug delivery. Therefore, to effect a sustained delivery of one or more drugs, a combination of one or more inclusion complexes, one or more prodrugs, or combinations thereof can be used. Such compositions are another embodiment of this invention. For example, prodrugs comprising a pharmaceutical covalently bonded to a cyclodextrin via an ester could be mixed with prodrugs which comprise an amide bond. The ester bond would hydrolyze more quickly to release the drug, whereas the amide would hydrolyze more slowly, thereby effecting sustained release. Alternatively, prodrugs having different pendant arms could be used to effect different releases. Likewise, combinations of different inclusion complexes such as those comprising linked and modified cyclodextrins can be used. Combinations of inclusion complexes and prodrugs can also be used. Furthermore, two different drugs can be co-administered using such compositions.

Methods for treating a host animal, including a human, will comprise administering therapeutically effective amounts of the pharmaceutical compositions of this invention. Importantly, the use of inclusion complexes and pharmaceutical derivatives in accordance with this invention can markedly enhance the performance of many drugs, and therefore dosages may have to be lowered from the usual prescribed amounts to account for these improved properties. For example, improved solubility of a drug may lead to improve bioavailability, possibly resulting in the need for lower dosages to be given to the patent, thereby reducing toxicity. Similarly, improved stability will lead to improved bioavailability for drugs which undergo hydrolysis or destruction in the stomach. Conversely, higher dosages of drugs which attack the mucosal stomach lining and cause gastric irritation may now be possible without fear of severe complications.

The inclusion complexes and prodrugs of this invention may also be used to deliver any drug for which improved or consistant bioavailability is desired, for example, drugs which have inconsistant responses in some patients. Further cyclodextrin inclusion complexes can also improve, ameliorate or remove the taste of compounds, thereby rendering them more acceptable to the consumer. This can be especially helpful in the case of veterinary compounds, where improved taste can greatly facilitate administration to animals.

As previously mentioned, stability constants on the order of $10^3$ to $10^4$ $M^{-1}$ are generally required for acceptable delivery of drugs for which inclusion is desirable. It is believed that the inclusion complexes and cyclodextrin derivatives of this invention can provide stability constants of from about $10^3 M^{-1}$ to $10^5 M^{-1}$ or more, which will render the resulting inclusion complexes suitable for drug delivery. Preferred constants are those which are at least $10^4 M^{-1}$. Likewise, prodrugs having long half-lives in acidic environments will also be useful for delivering pharmaceutical agents, although those having shorter half-lives may be desirable in some cases.

Additionally, the cyclodextrin derivatives and inclusion complexes of this invention can also be used in chromatographic compositions. Cyclodextrins are chiral natural products and accordingly exist in one enantiomeric form, i.e., only shown for cyclodextrins when their chiral characteristics are being discussed, and consequently has not been previously used in this specification.) Therefore, the complexation of the (+) and (−) enantiomers of synthetic molecules of the cyclodextrin annulus results in two complexes which are diastereoisomers:

(+)-enantiomer.D(+)-cyclodextrin; and
(−)-enantiomer.D(+)-cyclodextrin.

These two diastereoisomeric complexes will differ in stability to an extent which is dependent on the magnitude of the interactions between the enantiomer and the (+)-cyclodextrin. If the D-(+)-cyclodextrin is chemically bound to a solid support, a new chromatographic composition is produced which, because of differing complexation stabilities with the bound D(+)-cyclodextrin, will separate the (+) and (−) enantiomers. Accordingly, another embodiment of this invention comprises the cyclodextrin derivatives of this invention bound to a solid support. The resulting chromatographic compositions are suitable for the separation of enantiomers on both an analytical and commercial scale. An inclusion complex of this invention, when bound to a support, is also an embodiment.

For example, the chromatographic materials of this invention can be used to produce compounds such as L-amino acids (e.g., monosodium glutamate) and L-malic acid which are currently produced on a worldwide scale of millions of tons per month using enzyme catalyzed processes. Separation using cyclodextrins can be advantageous because they can be easier than enzymes to handle on an industrial scale, and because of the relatively greater costs of producing enzymes.

Thus, chromatographic compositions in accordance with this invention comprise at least one inclusion complex or cyclodextrin derivative of this invention bound to a solid support via a suitable linking or spacer group. For example, α-, β-, and γ-cyclodextrins may be reached at one or more of their primary or secondary hydroxyl groups to form aminocyclodextrins, which can be used as the stationary phase, as a component of the stationary phase, or as an added component to a mobile phase used in the separation of enantiomers in chiral chromatography. The linked cyclodextrins of this invention can be attached to the support by a linking or spacer group which directly links the support or a C2, C3 or C6 position of a linked cyclodextrin, or by a linking or spacer group that covalently bonds the support to the linking groups of the linked cyclodextrins.

Figure 13:
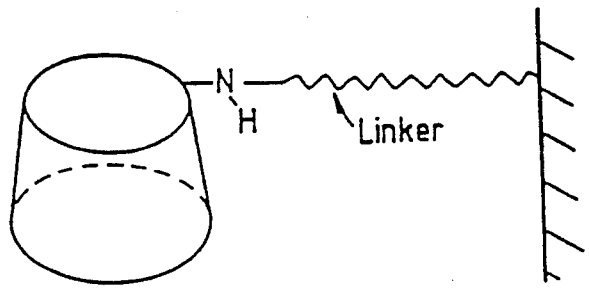
FIG. 13 illustrate a chromatographic composition in accordance with this invention.

Suitable solid supports are, for example, cellulose-based supports. Suitable linking or spacer groups are similar to those used to link cyclodextrins. An example of such a chromatographic composition is illustrated in FIG. 13.

In a manner similar to the formation of prodrugs, this invention also provides a process for separating a racemic mixture of enantiomers. In the process, the racemic mixture reacted with a quantity of cyclodextrin derivative to covalently bon the enantiomers of the racemic mixture to the cyclodextrin derivative to form diastereoisomeric cyclodextrin-enantiomer derivatives. The different diastereo-isomeric cyclodextrin-derivatives will have different properties and thus can be separated by conventional means. The covalent bond of each separate derivative can then be broken to yield each separated enantiomer in solution with the cyclodextrin. The enantiomers can then be isolated from the cyclodextrin using standard work-up techniques. In this process, it may also be helpful to first "protect" the hydroxyls of the cyclodextrin to render the cyclodextrin polar and thus more easily separable. If the hydroxyls are protected, it may be desirable to deprotect prior to the step of breaking the covalent bond (e.g., hydrolysis).

Formation of an ester or amide linkage may be desirable because such linkages can be broken by simple acid hydrolysis, thereby yielding the separated enantiomer in solution. It will be appreciated that the enantiomers of the racemic mixture may require some initial modification to enable them to form ester or amide linkages. However, given the guidance of this disclosure and the prior art, such modication will be within the ordinary skill of the art.

IV. Synthetic Procedures and Intermediates

This section provides synthetic procedures for preparing the various cyclodextrin derivatives and intermediates which can be used in accordance with this invention.

A. Preparation of Cyclodextrin Intermediates Substituted at C2, C3 or C6 with a Leaving Group Several possible synthetic routes for preparing cyclodextrin-leaving group intermediates are provided below. For purposes of illustration, the syntheses will be discussed using p-toluenesulfonate which is the preferred leaving group (See step A of Scheme 1 below). However those skilled in the art will appreciate that other leaving groups such as mesylates and other sulfonates, and iodides can be (and have been) formed by similar procedures, and it is likely that these can also be successfully utilized as intermediates.

Scheme 1

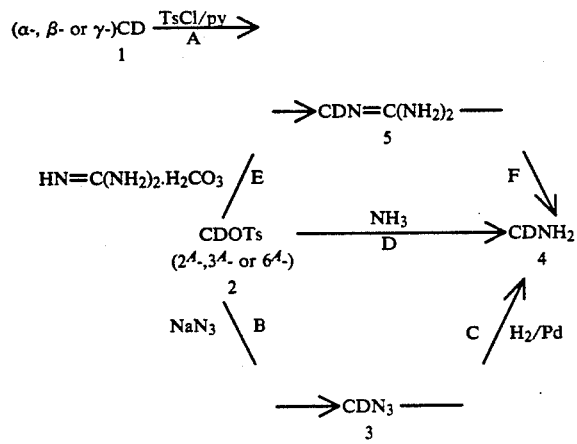

TsCl = p-toluenesulfonyl chloride
py = pryidine

1. The $6^A$-O-p-Toluenesulfonyl-Cyclodextrins

These cyclodextrins have the toluenesulonate substituted at the C6 carbon (i.e., $6^A$-O-tosyl cyclodextrins). $6^A$-O-Toluene-sulfonyl-α-cyclodextrin ($6^A$-CDOTs, 2) can be prepared by the method of Melton et al.; *Carbohydrate Research*, 18, (1971), 29–37. However, it has been found that the relative quantities of the reactants and the concentration of the reaction mixture can be altered to obtain the maximum yield of $6^A$-O-p-toluenesulfonyl-α-cyclodextrin for the purity of the solvents and reactants used. The preferred values are provide in the Examples which follow.

Workup procedures can also be altered from that described by Melton et al. For example, the reaction mixture can be poured into a large volume of cold acetone or other suitable solvent and the white precipitate collected by filtration or centrifugation and decantation, whereas Melton, et al. remove the solvent as an azeotrope with water by distillation under reduced pressure. The resulting solid or viscous liquid can be triturated with acetone or the suitable solvent and other solid collected by filtration or centrifugation. The crude product is advantageously purified to remove unreacted cyclodextrin and multi-p-toluenesulfonates which are less easily removed later in syntheses requiring $6^A$-O-p-toluenesulfonyl-α-cyclodextrin as an intermediate.

Surprisingly, it has been found that it is possible to effect an unexpectedly highly efficient purification of monosubstituted cyclodextrins such as $6^A$-O-p-toluenesulfonyl-α-cyclodextrin from mixtures of mono-substituted cyclodextrins, unsubstituted cyclodextrins and multisubstituted cyclodextrins, by using reverse phase chromatography. In this procedure, a sample of crude $6^A$-O-p-toluenesulfonyl-α-cyclodextrin is loaded onto a reverse phase column in a polar solvent. Unreacted α-cyclodextrin and materials of higher polarity than $6^A$-O-p-toluenesulfonyl-α-cyclodextrin are removed from the column by elution with this polar solvent. $6^A$-O-p-Toluenesulfonyl-α-cyclodextrin is then collected from the column using the same solvent or less polar solvent and then higher substituted and less polar materials are removed from the column by elution with a still less polar solvent. Surprisingly, it has been discovered that it is possible to load far more material onto the column, and still effect purification of the required component, than would normally be considered possible. Normally, the maximum weight of mixture per packed column volume that can be separated using a reverse phase column is less than about 1 g/100 ml per packed column volume. (For example, Murakari et al. *Tetrahedron Lett.* 28, (1987), 321–327, loaded 140 mg of crude $2^A$-O-p-toluene-sulfonyl-β-cyclodextrin ($2^A$-CDOTs) onto a RP8 column—an estimated mass to volume ratio of only 1 g/1000 ml per packed column material). However, it has been discovered that monosubstituted cyclodextrin can be separated by loading mixtures in amounts greater than about 1 g/100 ml, 1 g/20 ml and even 1.25 g/10 ml per packed column volume. In fact, amounts of up to about 1.8 g/10 ml per packed column volume can be efficiently separated without contamination of the eluted fractions with the unsubstituted and multisubstituted cyclodextrins. Beyond about 1.8 g/10 ml some multisubstituted cyclodextrin may contaminate the monosubstituted fraction. To carry out the separation, a C18 Reverse Phase column is preferred. For example, up to about 6.6–7.0 g of crude $6^A$-O-p-toluenesulfonyl-α-cyclodextrin can be dissolved in a minimum quantity of 30% aqueous methanol and loaded via the pump onto a 19×150 mm C18 μ-Bondapack HPLC column (an estimated mass to volume ratio of 1 g per 6.5 cm³ of column material). This can be eluted with 30% aqueous methanol at 15 ml/minute to give pure fractions of α-cyclodextrin and $6^A$-O-p-toluene-sulfonyl-α-cyclodextrin. The column is then washed with methanol and the multi-O-p-toluene-sulfonyl-α-cyclodextrins can be isolated.

Quantities of a di-O-p-toluenesulfonyl derivative of α-cyclodextrin have also been isolated using repeated Sephadex chromatography. An aqueous solution of the crude product is applied to a Sephadex G15 column and eluted with water. Fractions are collected. Those fractions containing any di-O-p-toluenesulfonyl derivative of α-cyclodextrin are evaporated to a small volume and reapplied to the column. The column is again eluted with water. This procedure is repeated until pure fractions of the di-O-p-toluenesulfonyl derivative are obtained. Conditions can be altered to increase the yield of multi-O-p-toluenesulfonyl derivative up to and including the hexa-O-p-toluenesulfonyl derivative (all primary positions): for example, see the procedures described in Umezawa et al.; *Bull. Chem. Soc. Jpn.* 41, (1968), 464–468.

The corresponding $6^A$-O-p-toluenesulfonyl-β-cyclodextrin can be prepared using the method of Melton et al. However, it has been discovered that far higher reaction mixture concentrations can be used and better yields of $6^A$-O-p-toluenesulfonyl-β-cyclodextrin obtained. This can be substantially purified by recrystallization so that further reactions can be carried out on this partially purified material. Very pure $6^A$-O-p-toluenesulfonyl-β-cyclodextrin can be obtained by reverse phase chromatography as is described for $6^A$-O-p-toluenesulfonyl-α-cyclodextrin. It is expected that $6^A$-O-p-toluenesulfonyl-γ-cyclodextrin may be prepared and purified in an similar manner.

In the industrial scale-up of this process, the purity and water content of the reagents becomes more critical. It has been discovered that the percentage of water is a result-determinative variable: too little water in the β-cyclodextrin or solvent can cause excessive quantities of multi-O-p-toluenesulfonate derivatives to be formed, whereas too much water can cause a drastic lowering of the yield. An acceptable level of water in the solvent is about 0.02% and in the β-cyclodextrin it is about 10%. Other procedural changes can also be made. Precipitation of the product during workup can be better effected using ether-acetone mixtures rather than acetone alone. The resulting suspension should be left to settle to allow for easier decantation and filtration. There may have to be less material per packed column volume loaded onto a reverse phase column for efficient chromotography. Process chemists and engineers designing the scale-up may recognize other changes that can be made. Examples 1,4 and 5 illustrate the scale-up procedure for preparing $6^A$-O-p-toluenesulfonyl-α-cyclodextrin and $6^A$-O-p-toluenesulfonyl-β-cyclodextrin.

2. The $2^A$-O-p-Toluenesulfonyl-Cyclodextrins $2^A$-O-p-toluenesulfonyl-cyclodextrins (i.e., the $2^A$-O-tosylcyclodextrins) can be prepared by reaction of an active ester of p-toluenesulfonate with a cyclodextrin in DMF and aqueous carbonate buffer. See, for example, Breslow, et al.; *Tetrahedron Lett.* 23, (1982), 3451. Further cyclodextrins can be monotosylated at a C2 carbon of cyclodextrin using a tin reagent, as described by Murakami, et al.; *Tetrahedron Lett.* 28, (1987), 321.

Reverse phase chromatography, and particularly where the column has been loaded with much more material than would be generally acceptable, as described above for $6^A$-O-p-toluenesulfonyl-α-cyclodextrin, should be an efficient method for the purification of this material.

3. The $3^A$-O-p-Toluenesulfonyl-Cyclodextrins

There are a number of reports in the literature relating to preparation of $3^A$-O-p-toluenesulfonyl-cyclodextrins ($3^A$-CDOTs); for example, Hattori et al.; *J. Am. Chem. Soc.* 97, (1975), 4432–4434 and Fujita et al.; *J. Am. Chem. Soc.*, 108, (1986), 2030–2034. It is noted, for example, that there has been some confusion regarding the position of substitution of the p-toluenesulfonate in the literature, and retractions have been made. For example, Breslow, et al.; *Tetrahedron Lett.* 23, (1982), 3451 disagrees with Hattori's et al.; *J. Am. Chem. Soc.* 97, (1975), 4432–4434 claim to have $3^A$-O-p-toluenesulfonyl-cyclodextrin. However other more recent claims have been made to $3^A$-O-p-toluenesulfonyl-cyclodextrin and other C3 sulfonates; Fujita et al.; *Tetrahedron Lett.* 25, (1984), 5673–5676 and Fujita et al.; *J. Am. Chem. Soc.* 108, (1986), 2030–2034.

Although the Examples which follow this section illustrate this invention as it pertains to $6^A$-O-p-toluenesulfonyl-cyclodextrins, both secondary O-p-toluenesulfonyl derivatives ($2^A$-O-p-toluenesulfonyl-cyclodextrins and $3^A$-O-p-toluenesulfonyl-cyclodextrins may be utilized to produce the corresponding secondary cyclodextrin derivatives. Persons skilled in the art will appreciate, however, that synthetic routes to $2^A$-O-p-toluenesulfonyl-cyclodextrins and $3^A$-O-p-toluenesulfonyl-cyclodextrins, and the corresponding desired cyclodextrin derivatives, may be different than routes to $6^A$-O-p-toluenesulfonyl-cyclodextrins and corresponding desired derivatives.

For example, $3^A$-O-p-toluenesulfonyl-cyclodextrins may be less desirable intermediates than the cyclodextrin mannoepoxides (prepared as described by Breslow et al.; *J. Am. Chem. Soc.* 105, (1983), 1390–1391 and references therein). As another example, it is known that the $2^A$-O-p-toluenesulfonate is not displaced by some nucleophiles (Murakami et al.; *Tetrahedron Lett.* 28, (1987) 321), and thus one skilled in the art may have to routinely experiment with several alternative nucleophiles to determine the best synthesis. However, one having ordinary skill in this art, guided by this disclosure and the published literature, will be able to devise suitable synthetic procedures for making the desired conversion.

B. Preparation of $2^A$-Azido-$2^A$-Deoxy-Cyclodextrin; $3^A$-Azido-$3^A$-Deoxy Cyclodextrin and $6^A$-Azido-$6^A$-Deoxy Cyclodextrin Intermediates Referring to Scheme 1, the conversion of the O-tosyl-cyclodextrin (CDOTs, 2) to the cyclodextrin-azide intermediate (CDN$_3$, 3) is shown in Step B. There are well established procedures for preparing $6^A$-azido-$6^A$-deoxy-cyclodextrins from the $6^A$-O-p-toluenesulfonyl-cyclodextrins, for example: Melton, et al;. *Carbohydrate Research* 18, (1971), 29–37. $6^A$-O-p-Toluenesulfonyl-α-cyclodextrin is dissolved in water with sodium azide and the solution heated until the reaction is complete. The solution is concentrated by distillation under reduced pressure and a quantity of 1,1,2,2-tetrachloroethane is added to precipitate the cyclodextrin material. The precipitate is collected by filtration or centrifugation and decantation and the 1,1,2,2-tetrachloroethane is removed by heating the precipitate in water and removing the organic layer. The azido-deoxy-cyclodextrin can be purified by chromatography on Sephadex G15 using water as eluant.

C. Preparation of $2^A$-Amino-$2^A$-Deoxy-Cyclodextrins; $3^A$-Amino-$3^A$-Deoxy-Cyclodextrins and $6^A$-Amino-$6^A$-Deoxy-Cyclodextrinxtrins Referring again to Scheme 1, amino-deoxy-cyclodextrins (CDNH$_2$, 4) can be prepared either from the corresponding azido-deoxy-cyclodextrins 3, or alteratively directly from the corresponding O-p-toluenesulfonyl-cyclodextrins 2. As previously discussed, the amino-deoxy-cyclodextrins 4 are useful by themselves in forming inclusion complexes, or as intermediates for other desired cyclodextrin derivatives.

1. Preparation of Amino-Deoxy-Cyclodextrin from Azido-Deoxy-Cyclodextrin

The procedure for preparing $6^A$-amino-deoxy-cyclodextrin from $6^A$-azido-$6^A$-deoxy-α-cyclodextrin is provided in Melton, et al.; *Carbohydrate Research* 18, (1971), 29–37. However, as discussed more fully below, it has been found that the $6^A$-amino-$6^A$-deoxy-α-cyclodextrin produced by the method of Melton et al can not be separated from the reaction mixture using ordinary separation techniques.

According to the method of Melton et al. $6^A$-Azido-$6^A$-deoxy-cyclodextrin has been converted to $6^A$-amino-$6^A$-deoxy-cyclodextrin by dissolving the azide in water and reacting the solution for an extended period of time with hydrogen in a Parr hydrogenator (i.e., H$_2$ under 30 psi pressure) in the presence of palladium black. The finely divided palladium is however very difficult to remove from the resulting solution. Filtration through a 0.2 μm filter does not remove all the powder catalyst.

Unexpectedly, it has been discovered that, after venting the hydrogen, a small volume of coagulating agent which can be a chlorinated hydrocarbon such as 1,1,2,2-tetrachloroethane can be added to coagulate the palladium black. This allows, after a short waiting period (e.g., 15 minutes), the solution to be easily filtered to remove palladium which otherwise cannot be completely removed. This process can likely also be used to isolate cyclodextrin derivatives from powder catalysts such as palladium, platinum or nickel. The solution can then be evaporated to yield the amino-deoxy-cyclodextrin. The above hydrogenation can also be carried out at ambient pressure, which might be preferred on an industrial scale.

Azido-deoxy-cyclodextrins hydrolyze slowly and the amines produced after hydrogenation are found to contain amounts of the parent cyclodextrin. The amino-deoxy-cyclodextrins may be purified by, for example, ion exchange chromatography. A solution of the amino-deoxy-cyclodextrin can be loaded onto a cation exchange column in the H+ form (e.g., Amberlite IRC 50, Amberlite CG 120, BioRex 70, RioRad AG50 WX-2). Non-amine materials are eluted from the column with water and the bound amines may then be eluted with hydrochloric acid, acetic acid or other acids to give the amino-deoxy-cyclodextrin salts or they may be eluted with ammonia solutions to give the free amino-deoxy-cyclodextrin. The amine salts would be expected to be more stable for storage as they are known to be resistant to oxidation and other degradative processes. The free amine can be released from the salt form by passing solutions of the amine through an anion exchange column in the OH− form. Alternatively the amino-deoxy-cyclodextrin can be isolated by loading onto a Bio-Rad Cellex P (hydrogen form) cation exchange cellulose column and eluting first with water to collect cyclodextrin and unreacted azide and then with 1M ammonia solution to collect amino-deoxy-cyclodextrin.

2. Preparation of Amino-Deoxy-Cyclodextrins from O-p-Toluenesulfonyl-cyclodextrins Alternatively, the amino-deoxy-cyclodextrin $\underline{4}$ can be formed directly from the O-p-toluenesulfonyl-cyclodextrins $\underline{2}$ by displacement of p-toluenesulfonyl with ammonia. This synthetic route may be preferable, especially on an industrial scale, to reduction of the azide because better and more pure yields might be obtained, less explosive reagents are being used and there is one less step in the reaction sequence. Three variations which illustrate this are as follows:

i. The O-p-toluenesulfonyl-cyclodextrin is dissolved in concentrated aqueous ammonia solution and the reaction mixture is stirred until all of the O-p-toluenesulfonyl-cyclodextrin has been consumed. One problem with this procedure, however, is the competition by hydroxide to hydrolyze the O-p-toluenesulfonyl-cyclodextrin derivative to the parent cyclodextrin. Pure amino-deoxy-cyclodextrin can be isolated after evaporation of the solvent and purification by the procedures outlined above.

ii. The O-p-toluenesulfonyl-cyclodextrin may be reacted with liquid ammonia either at atmospheric pressure (temperatures less than −33° C.) or at higher pressures in a bomb or similar apparatus. This procedure avoids the competing hydrolysis reaction and yields the pure amino-deoxy-cyclodextrin on evaporation of the ammonia.

iii. The O-p-toluenesulfonyl-cyclodextrin may be dissolved in a suitable non-nucleophilic solvent such as DMF and saturating the solvent with ammonia. Ammonia gas can be passed through the solvent at various temperatures determined to give the most efficient conversion to the amine for each O-p-toluenesulfonyl-cyclodextrin. Removal of the solvent will yield the amino-deoxy-cyclodextrin.

In another alternate synthesis, an amino-deoxy-cyclodextrin $\underline{4}$ can also be made from the corresponding O-p-toluenesulfonyl-cyclodextrin $\underline{2}$ (or cyclodextrin-leaving group intermediate) via a cyclodextrin-guanidine intermediate (CDN=C(NH$_2$)$_2$, $\underline{5}$) as illustrated in Steps E and F of Scheme 1. For example, 6$^A$-O-p-toluenesulfonyl-β-cyclodextrin (1 g, 1 mole equivalent) and from about 2 equivalents to about 10 equivalents preferably about 6 equivalents of guandine carbonate (((NH$_2$)$_2$C=NH)$_2$.H$_2$CO$_3$) can be heated in dry DMF (from about 1 ml.g$^{-1}$ to about 10 ml.g$^{-1}$ preferably about 1 ml.g$^{-1}$) and heated at from about 65° C. to about 120° C. preferably at about 100° C. overnight. The precipitate that forms by the addition of hot ethanol (50 ml), can be collected, redissolved in water and precipitates again with ethanol. The collected precipitate can be dissolved in hot aqueous KOH (2 g in 10 ml) and refluxed overnight. Ammonia is given off. The crude 6$^A$-amino-6$^A$-deoxy β-cyclodextrin can be precipitated with ethanol, redissolve in water and again precipitated with ethanol to yield 800 mg of 6$^A$-amino-6$^A$-deoxy-β-cyclodextrin.

D. Cyclodextrins Substituted with Pendant Arms

A cyclodextrin (α-,β- or γ-) or a simple derivatized cyclodextrin (where at least one cyclodextrin hydroxyl group has been substituted with, or transformed into, a different functional group or leaving group) can be made to react with another species (i.e., atom or molecule) so that the cyclodextrin becomes substituted with a pendant arm. This pendant arm can contain functional groups allowing for further elaboration of the molecule or for association with an included molecule. A functional group or leaving group attached to the cyclodextrin can be at any of the C2, C3 or C6 carbons of cyclodextrin and the pendant arm can be attached to cyclodextrin at any of these positions.

In cases where a pendant arm is connected to a cyclodextrin via a hydrolyzable linking group such as an ester or an amide, it is possible that the linking group can by hydrolyzed to return the pendant arm to its original form. In cases where the pendant arm is the residue of a pharmaceutical, agricultural, herbicidal, pesticidal, cosmetic or personal care agent, the agent is made available in an active form by hydrolysis. Covalently linking any of these agents, either directly or via an already existing pendant arm, onto an otherwise substituted or unsubstituted cyclodextrin provides derivatives of the agent with improved stability and/or delivery properties. Where a pharmaceutical agent is covalently linked, either directly or via an already existing pendant arm, to an otherwise substituted or unsubstituted cyclodextrin that derivative is termed a "prodrug." A prodrug can thus be thought of as a species of the genus comprising cyclodextrins substituted with pendant arms.

Hence, much of the following chemistry and principles of preparing pendant arm cyclodextrins can also be applied to preparing prodrugs. Thus, if a functional group (X) reacts with a different functional group (Y) to yield (Z), then if functional group (X) is attached to a cyclodextrin (CD-X), it will likely react with a functional group (Y) that is part of a pharmaceutical agent (Y-DR) to give a prodrug (CD-Z-DR) in which the pharmaceutical agent is covalently bonded to the cyclodextrin. A similar reaction will likely occur using similar conditions if the former functional group (X) is instead part of an already existing cyclodextrin pendant arm (CD-Pendant-X) to yield a prodrug where the drug is attached to the already existing pendant arm of the cyclodextrin (CD-Pendant-Z-DR). (That is, if CD-X+Y-DR→CD-Z-DR, then it is likely that CD-Pendant-X+Y-DR→CD-Pendant-Z-DR).

Still further, if a functional group (X) attached to a cyclodextrin (or to an existing cyclodextrin pendant arm) reacts with a functional group (Y) that is instead part of a pharmaceutical agent, then a similar reaction will likely occur using similar conditions if the former functional group (X) is part of the pharmaceutical agent and the latter functional group (Y) is attached to the cyclodextrin. (That is, if CD-X+Y-DR→CD-Z-DR, then it is likely that CD-Y+X-DR→CD-Z'-DR).

Accordingly, a pharmaceutical can be attached to an already existing pendant arm of a cyclodextrin to form a prodrug in two ways: (1) the pharmaceutical agent may be reacted with a pendant arm cyclodextrin to form the prodrug; or (2) a pendant arm can instead be attached to the drug, and the pendant arm is then reacted with cyclodextrin or a simple derivatized cyclodextrin to form the prodrug. (That is, either (1) CD-Pendant-X+Y-DR→CD-Pendant-Z-DR, or (2) CD-X'+Y'-Pendant-Z-DR→CD-Pendant-Z-DR). To ensure that a minimum of unwanted by-products are produced, the synthesis used should be determined according to the functional groups present on the cyclodextrin, the pendant arm and the pharmaceutical agent.

In any reaction to form a pendant arm cyclodextrin, a number of isomers might be formed. These include diastereoisomers, geometric isomers and structural isomers. In many cases it will be possible to separate these isomers using physical and chromatographic techniques. Cyclodextrins are available as enantiomers and, therefore, reaction of a cyclodextrin with a racemic mixture of a chiral molecule will produce a diastereomeric mixture of a pendant arm cyclodextrin. In some cases it will be possible to separate this mixture. If the link between a cyclodextrin and its pendant arm is capable of being hydrolyzed to give the chiral molecule in its original form, then this becomes a method of producing enantiomerically pure chemicals.

For example, the two isomers of the prodrug of Ibuprofen 6$^4$-O-p-($\alpha$-methyl-4-isobutylphenylacetyl)-$\beta$-cyclodextrin can be silylated (using, for example, t-butyldimethylsilylchloride, thexyldimethylsilylchloride or thexyldimethylsilyltriflate) using known procedures and the derivatized isomers separated on a silica gel column using, for example, chloroform or petroleum ether - chloroform gradient elutions (see Example 26). The pure silylated prodrug is then hydrolyzed and purified using known procedures such as treatment with methanolic hydrochloric acid or with fluoride ion (e.g., tetra-n-butyl-ammonium fluoride/tetrahydrofuran). The isomers can then be deprotected and identified.

E. Preparation of Cyclodextrins Substituted with Pendant Arms Linked via an Amine Any primary or secondary amine (NR) can replace a suitable leaving group (L) attached to cyclodextrin (CD-L) by a substitution reaction to give a pendant arm cyclodextrin where the pendant arm is attached to the cyclodextrin by an amine linkage (i.e., CD-L+NR→CD-NR). For example, the leaving group might be p-toluenesulfonate (OTs), so that CDOTs+NR→CD-NR. Certain tertiary amines may also be used: see, for example, Matsui et al.; Bull. Chem. Soc. Jpn., 51, (1978), 3030. Several amine linked pendant arm cyclodextrins (CD-NR) have been reported, and are reviewed by Croft et al.; Tetrahedron, 39, (1983), 1417–1474, and prepared as described by references cited therein.

Typical reaction procedures involve reacting an O-p-toluenesulfonyl-cyclodextrin with an amine (which may be further substituted) using the amine as solvent and heating normally involves precipitating a crude product with a suitable solvent, for example, acetone, acetone - ether or certain simple primary alcohols, followed by collection of the precipitate by filtration or centrifugation and decantation. Purification might be achieved by recrystallization from aqueous alcohol. If it is not possible to use the amine as solvent, then typically an excess of the amine is dissolved in a minimum of suitable solvent, for example, DMF, HMPA, or diglyme. Workup procedures are similar. In all cases, best yields are obtained using anhydrous O-p-toluenesulfonyl-cyclodextrin, amine and solvent.

For example, O-p-toluenesulfonyl-$\alpha$-cyclodextrin is dissolved in the diaminobutane and heated from about 50° C. to about 120° C., preferably at about 70° C., and for from about 1 hour to about 24 hours, preferably until the reaction is complete. Acetone or other suitable solvent such as a C1 to C6 primary alcohol is added to precipitate the product which is collected by centrifugation or filtration, and washed with further quantities of acetone. The product is typically recrystallized from aqueous alcohol.

The amine may also be part of a heterocyclic ring. For example, O-p-toluenesulfonyl-$\beta$-cyclodextrin and piperazine hexahydrate (from about 1 equivalent to a large excess, preferably about 10 equivalents) is dissolved in a suitable solvent, for example, DMF (about 1 ml per gram of O-p-toluenesulfonyl-$\beta$-cyclodextrin). The reaction mixture is heated at from about 70° C. to about 150° C., preferably at about 120° C., and stirred until the reaction is complete. Pyridine may be added or used alone as solvent in cases where the free amine is expensive and therefore the molar excess of that amine in the reaction mixture is insufficient to react with all the p-toluenesulfonic acid produced.

Work-up is by pouring the hot reaction mixture into excess acetone or alcohol solvent and treating the precipitate as above. The product is typically recrystallized from aqueous alcohol. With deactivated amines, such as anilines, longer reaction times and/or higher reaction temperatures than those suggested above may be required.

Where two reactive amine groups are present in a diamine, and where the cyclodextrin has been substituted with more than one p-toluenesulfonate or other leaving group, the product of the reaction between the diamine and the substituted cyclodextrin may contain two pendant arms or a diamine cap, or be a polymeric cyclodextrin, with a degree of polymerization of two or more.

Two methods for linking the pharmaceutical agent Ibuprofen to a pendant arm, which is in turn linked to cyclodextrin through an amine, are provided below and are more specifically described in the Examples which follow this Section. In the first method the reaction product of O-p-toluenesulfonyl-β-cyclodextrin and piperazine hexahydrate (6$^A$-deoxy-6$^A$-(1,4-diazacyclohexyl)-β-cyclodextrin), described above, is acrylated with an excess of the acid chloride of Ibuprofen (IbCl) in DMF - pyridine at room temperature overnight. Workup and recrystallization gives the prodrug. In the second method O-p-toluenesulfonyl-β-cyclodextrin is reacted with the amide formed between IbCl and piperazine, (which compound may be readily prepared by the addition of IbCl to an excess of anhydrous piperazine, using a procedure similar to that described in Example 48, using piperazine instead of 1,4-diaminobutane) in dry pyridine at from about 70° C. to about 80° C., overnight. Workup and recrystallization yield the same prodrug.

Where the pendant arm has more than one reactive amine, it is often preferable to make a prodrug according to the second method above. For instance, 6$^A$-deoxy-6$^A$-(4-aminobutylamino)-β-cyclodextrin reacts with acrylating agents such as IbCl to give a mixture of products. Therefore, prodrugs such as 6$^A$-deoxy-6$^A$-(4-(α-methyl-4-isobutylphenylacetamido)butylamino)-β-cyclodextrin (Ibuprofen linked to 6$^A$-deoxy-6$^A$-(4-aminobutyl-amino)-cyclodextrin via an amide function) are most conveniently prepared by the second method.

Scheme 2

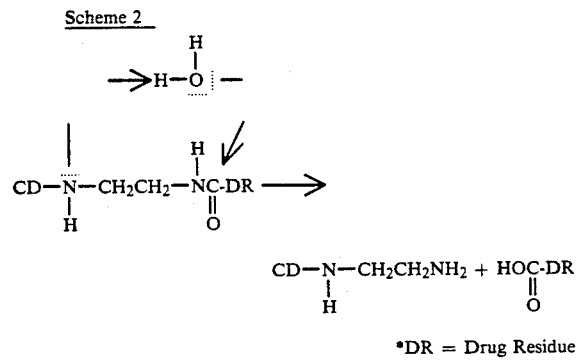

*DR = Drug Residue

Scheme 2 illustrates the hydrolysis of a prodrug. The prodrug comprises a drug residue linked by an amide to a pendant arm substituted via an amino group on a cyclodextrin. This prodrug will readily hydrolyze where water is present, in what is presumably a base-catalyzed reaction promoted by the secondary amine. Hydrolysis release the drug in its active form with the concomitant reformation of the aminoalkylamino-cyclodextrin.

F. Preparation of Cyclodextrins Substituted with Pendant Arms Linked via a Sulfur A pendant arm may also be substituted onto a cyclodextrin via a sulfur linkage. The pendant arm itself may have further functional groups on its allowing for further elaboration or for associations with an included molecule. Several methods of performing this have been described in the literature and are described below.

1. Reaction of Thiol Salts with Deoxy-Iodo-Cyclodextrins

The sodium salt of a thiol will react with a deoxy-iodo-cyclodextrin when heated in dry DMF under argon to give the corresponding thio substituted cyclodextrin according to a procedure similar to that of Tabushi et al.; *J. Am. Chem. Soc.* 108, (1986), 4514–4518.

2. Reaction of Thiols with Cyclodextrins Epoxides

A thiol will react with an epoxide of a cyclodextrin when heated in aqueous ammonium bicarbonate to give the corresponding doubly inverted thio substituted cyclodextrin according to a procedure similar to that of Breslow et al.; *J. Am. Chem. Soc.* 105, (1983), 1390–1391.

G. Preparation of Cyclodextrins Substituted with Pendant Arms Linked via an Ester Esterification of cyclodextrin molecules by transesterification has been reported in the literature, for example, Croft et al.: *Tetrahedron*, 39, (1983), 1417 and references thereon. This normally involves the reaction of activated esters (for example, m-nitrophenyl esters) under basic conditions for esterification at C2 and C3 carbons. Under such reaction conditions, these products normally undergo subsequent hydrolysis to yield cyclodextrin and carboxylic acid. Thus purification of the cyclodextrin esters often gives low yields. See, for example, Van Etten et al.; *J. Am. Chem. Soc.*, 89 (1967), 3242 and references cited therein; Van Etten et al.; ibid., 89, (1967), 3253; Kurono et al., *Bioorg. Chem.*, 5, (1976), 393 and others.

However, it has been discovered that it is possible to esterify a cyclodextyrin at the desired hydroxyl using milder conditions and in which the product esterified cyclodextrins are more stable. Further, these conditions will also provide a good yield of the esterified cyclodextrin. Thus, the sodium, potassium, cesium or rubidium salt of a carboxylic acid (MOCOR) can be reacted with a O-p-toluenesulfonyl-cyclodextrin (CDOTs) or with another cyclodextrin substituted with a suitable leaving group (cyclodextrin-leaving group intermediate) to give an ester linked pendant arm (that is, CDOTs+MOCOR→CDOCOR). Although sodium salts might be least expensive, cesium salts might be used in the case of a particularly sensitive reaction. For example, cesium might be used in a reaction that is sensitive to heat in order to increase yields by lowering the decomposition of the product, cyclodextrin and/or drug. If the carboxylic acid function or its salt is part of a pharmaceutical agent, a prodrug can be made by this method. This procedure is illustrated as follows.

A salt of the carboxylic acid is first made. 6$^A$-O-p-Toluenesulfonyl-β-cyclodextrin (2.5 g) is dissolved with from about 1 equivalent to about 10 equivalents, and preferably about 1.1 equivalents of cesium (+)-α-methyl-6-methoxy-2-naphthyl-acetate (cesium salt of Naproxen) in dry DMF or other aprotic solvent such as DMSO. The mixture is heated to from about 65° C. to about 140° C., preferably about 100° C., for about 18 hours or until completion of the reaction. Standard workup (for example, by precipitation of the product with acetone and filtration) and purification (for example, on a Sephadex column) will give good yield of the prodrug 6$^A$-O-((+)-α-methyl-6-methoxy-2-naphthylacetyl)-β-cyclodextrin.

As before, the carboxylic acid salt may contain other functions for further elaboration of the pendant arm or for association with an included molecule. For example, cyclodextrins substituted with acrylates in secondary positions have been prepared by Harada et al.; *Macromolecules*, 9, (1976), 701–704, by reaction of m-nitrophenylacrylate with cyclodextrin in basic conditions and the resultant O-acrylylcyclodextrins, $3^A$-O-acrylylcyclodextrins and $6^A$-O-acrylylcyclodextrins used to make a cyclodextrin polymer. However, it is preferred to prepare $2^A$-O-aryl-cyclodextrins, $3^A$-O-acrylyl-cyclodextrins by a substitution reaction of the corresponding O-p-toluenesulfonyl-cyclodextrin with an acrylate salt such as cesium acrylate, potassium acrylate or sodium acrylate.

For example, $6^A$-O-p-toluenesulfonyl-$\beta$-cyclodextrin can be stirred with from about 1 equivalent to about 10 equivalents, preferably about 1.1 equivalents, of cesium acrylate in dry DMF and heated from about 65° C. to about 140° C., preferably about 100° C., for about 18 hours or until the reaction is complete. Acetone is added to precipitate the product. Normal workup and purification measures will produce $6^A$-O-acrylyl-$\beta$-cyclodextrin in good yield.

The foregoing paragraphs have described the reaction of a pendant arm that contains a carboxyl group (in salt form) with a cyclodextrin-leaving group intermediate (e.g., O-tosyl cyclodextrin) to form an ester. However, a different ester can be prepared by reacting a pendant arm that contains an alcohol with a cyclodextrin that contains a carboxylic acid derivatized to undergo substitution. A carboxylic acid derivatized to undergo substitution is a carboxylic acid that has been derivatized to produce an acid halide, symmetric or asymmetric acid anhydride or an ester such that the derivatized carboxylic acid will, given the proper reaction conditions, undergo substitution. A dicarboxylic acid which is derivatized to undergo substitution has each carboxylic acid function derivatized as above. For example, an ester linked pendant arm can be produced by reacting $5^A$-demethyl-$6^A$-deoxy-$5^A$-carboxy-cyclodextrin (prepared by oxidation of $5^A$-demethyl-$6^A$-deoxy-$5^A$-formyl-cyclodextrin which is prepared, for example, according to the method of Gibson et al. *Can. J. Chem.*, 52, (1974), 3905), which has been derivatized to undergo substitution, with an alcohol. Alternatively, the ester linked pendant arm can be prepared by reacting a salt of $5^A$-demethyl-$6^A$-deoxy-$5^A$-carboxy-cyclodextrin with a tosylate.

H. Preparation of Cyclodextrins Substituted with Pendant Arms Linked via an Amide A pendant arm can be substituted onto a cyclodextrin via an amide function. Umezawa et al.; *Bull. Chem. Soc. Jpn.*, 41, (1968), 464–468 prepared $6^A,6^B,6^C,6^D,6^E,6^F$-hexaacetamido-$6^A,6^B,6^C,6^D,6^E,6^F$-hexadeoxy-cyclodextrin from a reaction of the corresponding $6^A,6^B,6^C,6^D,6^E,6^F$-hexaamino-$6^A,6^B,6^C,6^D,6^E,6^F$-hexadeoxy-$\alpha$-cyclodextrin with acetic anhydride in methanol. However, it has been found that by relying on the higher nucleophilicity of the amine over the hydroxyls it is possible to selectively react carboxylic acids derivativatized to undergo substitution (XCOR). For example, symmetric or asymmetric anhydrides, acid chlorides, and active esters (e.g., m-nitrophenyl esters) can be dissolved in a suitable solvent (e.g., methanol, DMF, DMSO) and reacted with cyclodextrin derivatives having an amino group or a substituted amino group substituted for at least one C2, C3 or C6 hydroxyl (CDN(R')H) to form amino-deoxy-cyclodextrins (CDN(R')COR). That is, CDN(R')H+XCOR→CDN(R')COR. In some cases the derivatized carboxylic acid will be non-selective and react with the cyclodextrin amine function to form amides, and also with the cyclodextrin hydroxyls to form esters. In such cases, it may be necessary to choose a less reactive carboxylic acid derivative; for example, an ester could be used instead of an acid chloride.

A carboxylic acid derivativatized to undergo substitution may also contain other functions for further elaboration of the pendant arm or for association with an included molecule. For example, the preparation of acrylamido-deoxy-cyclodextrins is possible by the reaction of the amino-deoxy-cyclodextrins and an acrylate derivativatized to undergo substitution such as acrylic anhydride, acrylyl chloride or $\mu$-nitrophenyl acrylate. For example, $6^A$-amino-$6^A$-deoxy-$\beta$-cyclodextrin is stirred with from about 1 equivalent to about 10 equivalents, preferably about 4 equivalents, of acrylic anhydride in methanol (or other suitable solvent) and stirred overnight or until completion of the reaction. Acetone is added to precipitate the product. Normal workup and purification will produce $6^A$-acrylamido-$6^A$-deoxy-$\beta$-cyclodextrin. This product may be used to link two or more cyclodextrins. Thus, $6^A$-acrylamido-$6^A$-deoxy-$\beta$-cyclodextrin can be dissolved in a suitable solvent and a radial initiator such as, for example, benzoyl peroxide or azosibutyronitrile, is added. The reaction mixture is heated and/or irradiated and after workup of the reaction mixture, a polymer of at least two cyclodextrin units and likely up to five cyclodextrin units will be formed.

An amide linked pendant arm can also be produced from a similar reaction of $5^A$-demethyl-$6^A$-deoxy-$5^A$-carboxycyclodextrin (prepared by oxidation of $5^A$-demethyl-$6^A$-deoxy-$5^A$-formylcyclodextrin which can be prepared, for example, according to the method of Gibson et al. *Can. J. Chem.*, 52, (1974), 3905), which has been derivatized to undergo substitution with an amine.

If a pharmaceutical agent has a carboxylic acid function, it can be derivatized to undergo substitution by making, for example, the symmetric anhydride of the pharmaceutical agent. A prodrug can then be made using the anhydride. For example, a mixture of $6^A$-amino-$6^A$-deoxy-$\beta$-cyclodextrin (850 mg) and the symmetric anhydride of Ibuprofen (from 1 equivalent to about 10 equivalents preferably about 1.1 equivalents) can be dissolved in methanol (from about 5 ml to about 100 ml, preferably about 20 ml) and stirred and heated at from about 10° C. to about 65° C., preferably at about room temperature overnight or until completion of the reaction. Workup by precipitation with acetone or suitable solvent and purification gives $6^A$-deoxy-$6^A$-($\alpha$-methyl-4-isobutyl-phenylacetamido)-$\beta$-cyclodextrin (a prodrug in which the drug is linked by an amide to the cyclodextrin).

F. Preparation of Drugs Covalently Linked to Cyclodextrin (Prodrugs)

Prodrugs may be prepared by reacting a pharmaceutical agent having a suitable functional group with a substituted or unsubstituted cyclodextrin. The pharmaceutical agent may be attached directly onto the cyclodextrin, or onto an already existing pendant arm of a cyclodextrin. As previously mentioned, a prodrug can be thought of as a species of pendant arm cyclodextrins, and therefore the chemistry described above also applies to preparing prodrugs. It should be kept in mind that certain pharmaceutical agents used in these reactions may contain certain functional groups which interfere with the reaction or which will be changed during the reaction. It might thus be necessary to protect these functional groups before covalent attachment of the pharmaceutical agent to the cyclodextrin, and to then remove the protection after the covalent attachment. Processes for protecting sensitive functional groups, reacting protected species, and then removing the protection are well known to those skilled in the art.

To form a satisfactory prodrug, the pharmaceutical agent must have a functional group capable of reacting with a functional group attached to cyclodextrin or to a cyclodextrin pendant arm. The covalent bond formed by reacting the two functional groups must, when broken, yield the drug in its active form. Suitable functional groups of a pharmaceutical agent include carboxyls (—COOH), thiols (—SH), aldehydes (—CHO), amines (—NH$_2$, —NH— and —N) and hydroxyl (—OH) or the salts of any of these functional groups. An illustration of some of the possible reactions using these functional groups is provided in Scheme 3.

There are many other possible covalent linkages that can be made between drugs with suitable functional groups and suitably functionalized cyclodextrins or pendant arms substituted onto the cyclodextrins. One having ordinary skill in this art will recognize other linkages that can be made using known chemistry, and which when broken, will yield the drug in active form.

The products formed by covalent attachment of pesticidal, agricultural, herbicidal, cosmetic or personal care agents are also of interest, and the procedures used parallel those for the prodrugs.

Scheme 3

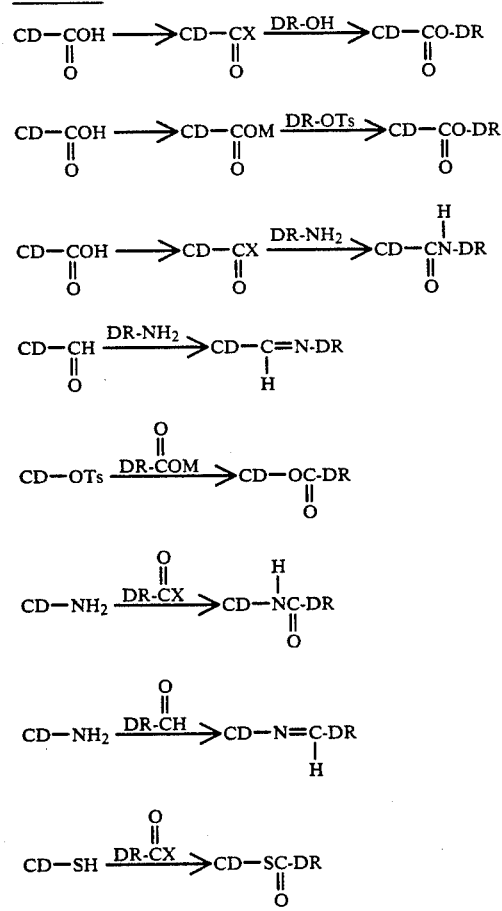

-continued

Scheme 3

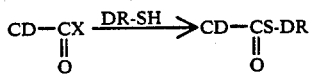

*DR - Drug Residue

J. Preparation of Linked Cyclodextrins

The linked cyclodextrins previously described can be prepared by either of the two processes that are illustrated in Schemes 4 and 5.

Scheme 4

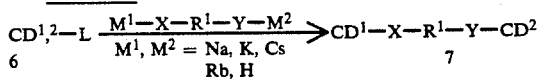

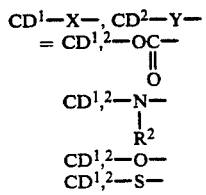

Process 1

Scheme 4 illustrates the first process in which at least one cyclodextrin-leaving group intermediate (CD$^{1,2}$—L, 6) (e.g., 6$^A$-O-p-toluenesulfonyl-cyclodextrin) is reached with a reactant of the formula M$^1$—X—R$^1$—Y—M$^2$ to yield a linked cyclodextrin of the formula CD$^1$—X—R$^1$—Y—CD$^2$ 7. R$^1$ and R$^2$ represent the same or different groups selected from substituted and unsubstituted: alkyl, alkenyl, alkynyl, cycloalkyl, cycloalkenyl, cycloalkynyl, aryl, heteroaryl and heterocyclyl. R$^1$ and R$^2$ may be further substituted by at least one group as defined by R$^1$ and R$^2$ or further functional groups, and R$^2$ can also be hydrogen.

The process of Scheme 4 parallels previously discussed processes such as that used to prepare cyclodextrins substituted with pendant arms linked via an ester (See Section IV.G.). For example, the salt (e.g., disodium, dipotassium, or dicesium) of a dicarboxylic acid) is mixed with 2 equivalents of cyclodextrin tosylate in DMF, and the reaction is stirred and heated for 24 hours. Workup and purification will yield the linked diester. No formation of the capped product is predicted and the conditions employed are equals enough that the esters will be isolable.

Scheme 5

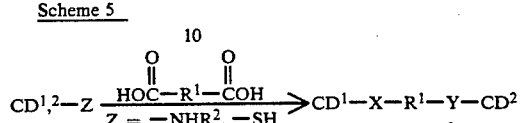

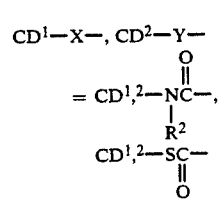

Process 2

Referring to Scheme 5, a second process for making a linked cyclodextrin of the formula $CD^1$—X—R$^1$—Y—$CD^2$ 9 is provided. The process comprises reacting a cyclodextrin acid ($ND^2C$—$R^1$—$CO^2H$, 10) that has been derivatized to undergo substitution, wherein $CD^1$—X—, $CD^2$—Y—, and Z are as shown, and $R^1$ and $R^2$ are as previously defined. This process parallels previously discussed processes such as that used to prepare cyclodextrins substituted with pendant arms linked via an amine (see Section IV.E.). Examples of suitable dicarboxylic acids include those such as succinic acid, glutaric acid and terephthalic acid, although many others can be chosen.

For example, if succinic acid is chosen as the dicarboxylic acid, and $6^A$-amino-$6^A$-deoxy-$\beta$-cyclodextrin is chosen as the cyclodextrin derivative of formula $CD^{1,2}$—Z, then the process can be as follows. From about 2 equivalents to about 10 equivalents, preferably about 2 equivalents, of $6^A$-amino-$6^A$-deoxy-$\beta$-cyclodextrin are stirred in DMF and about 1 equivalent of the m-nitrophenyl-diester of succinate is added in small portions over 12 hours. Upon completion, normal workup will provide the linked cyclodextrin as the major component of a complex mixture of products, including an amide-ester succinyl capped cyclodextrin. Although the reactivity of the amine on the cyclodextrin is so much higher than any hydroxyl on the cyclodextrin, once the succinyl has been attached to one cyclodextrin via an amide, proximity of the remaining ester to a cyclodextrin hydroxyl will cause formation of the amide-ester succinyl capped cyclodextrin to be competitive with formation of the linked cyclodextrins. Varying the concentrations and relative quantities of the reactants will alter the yields of the linked material and the range of products from competing reactions. For example, if 1 equivalent of $6^A$-amino-$6^A$-deoxy-$\beta$-cyclodextrin is stirred in DMF and 1 equivalent of the m-nitrophenyl-ester of succinate added in one portion, the yield of amide-ester succinyl capped cyclodextrin is increased. It may be important that the $6^A$-amino-$6^A$-deoxy-$\beta$-cyclodextrin is in its free form and not protonated or present as a salt. Addition of base such as triethylamine, or use of a more basic solvent such as pyridine may also improve yields.

For example, the diamide linked cyclodextrin may be produced from the reaction of cyclodextrin amines with dicarboxylic acids that have been derivatized to undergo substitution. The dicarboxylic acid can be, for example, succinic acid in which case, from about 2 equivalents to about 10 equivalents, preferably about 2 equivalents, of $6^A$-amino-$6^A$-deoxy-$\beta$-cyclodextrin can be stirred in DMF and 1 equivalent of the m-nitrophenyl-diester of succinate is added in small portions over 12 hours. Upon completion of the reaction, normal workup will provide the linked cyclodextrin as the major component of a complex mixture of products. Varying the concentrations and relative quantities of the reactants will alter the yields of the linked material and the range of products from competing reactions.

The following Examples are provided only to illustrate various embodiments of this invention, and do not in any manner limit this invention.

Examples 1 to 7 illustrate scaled-up production of the $\alpha$- and $\beta$-cyclodextrin amines. The quantities of reagents are reported as for a laboratory scale reaction or as for pilot scale.

EXAMPLE 1

Production of the $\beta$-Cyclodextrin Monotosylate

The raw materials for this synthesis are pyridine, $\beta$-cyclodextrin, p-toluene sulphonyl chloride and acetone. Initially, it has been discovered that the water content of pyridine used in the reaction is very important. The water helps retard the extent of the reactions; too much water results in no reaction, too little results in polytosylation.

Accordingly, Analytical Reagent (AR) grade pyridine is dried as follows. First, 4 Angstrom (or 3 Angstrom) molecular sieves are dried under Argon for at least about 18 hours at 250° C. The dried molecular sieves are added to the pyridine (200 ml of sieves per 2.5 liters of pyridine), and left for 48 hours. A moisture content of about 0.02% in the pyridine has provided acceptable yields of product results. The $\beta$-cyclodextrin need not be completely dried, with about 10% loss of moisture on drying being acceptable. The p-toluene sulphonyl chloride should be checked by batch trial, because impurities may cause the reaction to fail. Commercial grade acetone (<0.3% water content) is acceptable.

In the reaction, 518 g of $\beta$-cyclodextrin are added, with stirring, to 3850 ml of pyridine. When the $\beta$-cyclodextrin is dissolved the temperature will rise about 20° C. The solution should be slightly cloudy/opalescent, with no obvious solids. It is important that the resulting solution not be allowed to stand for any length of time because of risk of gelatinization. A tosyl chloride solution comprising 68 g of tosyl chloride in 150 ml pyridine is then gradually added to the $\beta$-cyclodextrin solution over a period of 45 minutes with stirring. Stirring is stopped when all of the tosyl chloride solution has been added. The reaction solution is then left to stand in a closed vessel overnight (16-20 hours). It is believed that less time may actually be required for the reaction, particularly if a higher temperature is used.

The reaction mixture is then added, with stirring, to forty liters of pre-chilled acetone (−20° C. overnight) over ten minutes. The mixture is then allowed to stand for approximately two hours to allow the precipitate to settle. The solution is then decanted by vacuum and the remaining solids are filtered by vacuum on a five liter Buchner. The cake is pressed well to express the pyridine. The precipitate is then resuspended (rather than washed on the filter) in two liters of room temperature acetone. The suspension is filtered, and the precipitate washed with a further two liter of acetone. A constant air flow is maintained through the filter cake using a vacuum, with continuous pressing of the cake to prevent channelling. The cake becomes friable in about one hour. It is believed that it is important to remove all pyridine as soon as possible. The precipitate is allowed to air dry overnight in a very thin layer in a fume cupboard. The precipitate is recrystallized with boiling distilled water (two liters for a 518 g scale reaction). It has been found that the reaction mixture must be heated to at least 95° C. to dissolve all of the precipitation. At less than about 95° C., all of the precipitate does not dissolve and product is lost. The hot mixture is immediately filtered without vacuum to prevent foaming. The filtrate is cooled to room temperature (15°-20° C.) to precipitate the product. The hot precipitate may be discarded. The precipitate that forms when the solution has been cooled is filtered off, and the mother liquor and precipitate are analyzed. The mother liquor is left to stand overnight at room temperature and any further precipitate that forms is filtered off. Again, both the mother liquor and precipitate are analyzed. The recrystallization step is repeated on the product obtained when the solution is first cooled, and possibly also on the product obtained when the solution is left to stand overnight, depending on the TLC result for that precipitate. During this second recrystallization step, the precipitate is fully dissolved and the hot filtration step is omitted. If necessary, recrystallization is repeated again until the amount of ditosylate is 5% or less. The crystals are then dried in vacuo at less than 45° C.

EXAMPLE 2

Production of 6-Azido-6-Deoxy-β-Cyclodextrin

The materials used in this step include the cyclodextrin monotosylate from the previous example, AR Grade Sodium Azide, and Laboratory Grade 1,1,2,2-Tetrachloroethane ("TCE"). TCE has a tendency to degrade, and care must be taken to ensure that the TCE has not become too acidic. If the acidity is greater than about 0.001%, then it will be necessary to wash to TCE with water until a satisfactory low acidity is obtained.

Nine liters of distilled water are heated to approximately 50° C., and 300 g of β-cyclodextrin monotosylate and 300 g of sodium azide are added to the heated water. It is noted that the sodium azide is in considerable excess, the amount not yet having been optimised. The solution is then heated with stirring to 90° C. (using a heated mantle) for 90 minutes, and a sample is analyzed. The reaction solution is then concentrated, in vacuo with a maximum vapor temperature of 35°-40° C., until the reaction solution is approximately one-sixth of its initial volume (1500 ml). During this step, care must be taken to not increase the vapour temperature above 35°-40° C. to avoid degradation. The solution is then cooled to room temperature. TCE (150 ml per 1500 ml concentrated batch volume) is added. The mixture is then agitated vigorously for approximately two minutes in a glass stoppered vessel to yield a white precipitate. The pressure in the vessel is released occasionally while agitating. It is important that sufficient agitation, not just stirring, is achieved to yield an emulsion. In small scale, the reaction vessel can be shaken, and in larger scale a high speed mixture with an emulsion head can be used. The reaction mixer is then allowed to stand for one hour, and the solids are collected by vacuum filtration. The solid material is then washed with small amounts of ice-cold water, for example, three times using 300 ml of water per batch. It is important to use as little water as possible because the product can be washed out. The filtration is repeated if more solid precipitates from the filtrate upon standing. Samples of the filtrates and the precipitates are analyzed. If necessary the TCE precipitation should be repeated as above. To remove the TCE impurities, add distilled water to the solid (approximately one liter) in a Buchi flask. The mixture is heated until the solid dissolves. The solution is then evaporated to dryness in vacuo (maximum vapor temperature 35°-40° C.). The steps of adding distilled water, heating and evaporating are repeated until all TCE is removed. Again, a sample is analyzed. The product is recrystallized by adding the minimum amount of boiling distilled water (approximately 750 ml per batch). The solution is heated with stirring until the product dissolves at near boiling temperature. The solution is cooled to ambient temperature, and then left at 4° C. overnight. The crystals that precipitate out are filtered off by vacuum and allowed to air dry. The product is then dried under vacuum at ambient temperature, and stored in a vacuum desiccator over $P_2O_5$. The filtrate should be analyzed and if necessary the precipitation step repeated.

EXAMPLE 3

Production of 6-Amino-6-Deoxy-β-Cyclodextrin

The materials for this reaction are then 6-azido-6-deoxy-β-cyclodextrin from the previous Example, palladium black and TCE. Again, it is important to check the acidity of the TCE and, if necessary, wash the TCE with water.

The 6-azido-6-deoxy-β-cyclodextrin is dissolved in water (770 mg of azide to 150 ml water), and if necessary, the solution may be heated gently to dissolve the azide. However, do not exceed 30° C. Palladium black is then added (250 mg per 770 mg of the azide). All air is then removed from the vessel. Hydrogenation is carried out for about 1-2 days in a stirred glass vessel at room temperature and at a slightly positive atmosphere to prevent air entry for safety reasons, (for example 2 cm of water greater than atmospheric pressure). Alternatively, a pressurized reaction can be carried out in a shorter time. Samples of the mixtures are analyzed after 12, 24, 36 and 48 hours to monitor the reaction. Hydrogen is vented using vacuum/$N_2$ purging cycles. The reaction mixture is transferred to a mixing vessel and TCE ia added, if necessary, to coagulate the palladium black (maximum 1 ml per 770 mg scale reaction). If TCE had been added, the mixture is stirred vigorously for about 30 seconds to form an emulsion and then allowed to stand for 15 minutes. The mixture is then coarsely filtered to remove the majority of the palladium black, and the mixture is evaporated to 1-2 liters. The mixture is filtered as required until the solutions. The mixture is filtered as required until the solution is completely clear and bright (eg. What man #1 or 190 42, followed by 0.45 μm membrane filter is necessary). The filtrate is then evaporated under vacuum to dryness at a vapor temperature less than 45° C. The filtrate is then redissolved in water and passed through a Biorad AG 50W X2 ion exchange column (200–400 mesh). The product cyclodextrin amine binds to the ion exchanger (in the hydrogen form) and the unbound cyclodextrin passes through. The column is flushed with water to remove unbounded cyclodextrin, and then the cyclodextrin amine product is eluted with ammonium hydroxide. While this separation procedure enables easy purification of the cyclodextrin amine product, significant quantities of the product can be lost unless the product is eluted with warm ammonium hydroxide. Thus, the column is heated to about 40° C. and flushed with 1 l Milli Q water to remove the cyclodextrin. The product is then eluted with 25% $NH_4OH$ (40° C.) of increasing concentration of up to 7.5 M until all the product has been recovered: e.g., 1 l of 0.5 M $NH_4OH$, 1 l of 1.0 M $NH_4OH$, 1 l of 3.0 M $NH_4OH$ and 1 l of 7.4 M $NH_4OH$ give near quantitative recovery of the product.

The eluted product is then dried under vacuum. If necessary the cyclodextrin amine is recrystallized from cold water to remove color. The product is stored over $P_2O_5$ in a vacuum desiccator. The product is not stable in solution and must be dried if it is to be held for any length of time.

EXAMPLE 4

Production of α-Ccylodextrin Monotosylate

The materials for preparing the Monotosylate include: α-cyclodextrin which does not require drying; p-toluene- sulphonyl chloride, which should be checked by batch trial to ensure sufficient purity; pyridine, which is dried as described above in Example 1; acetone, which does not require drying provided that the water content is less than 0.3%, and diethyl ether (anhydrous).

Two hundred grams of α-cyclodextrin are slowly added to 20 liters of pyridine, with stirring. The resulting solution should be faintly cloudy/opalescent. To this solution is added 200 g of tosyl choride with stirring until the solution becomes clear. The reaction solution is allowed to stand for two hours, and a sample is analyzed. The reaction mixture is slowly added, with stirring, to a solution comprising 150 liters of acetone and 25 liters of diethyl ether (prechilled to −8° C.). The mixture is then transferred to a 200 liter flask and left to stand for 1-2 hours to allow the precipitate to settle. The supernatant is decanted by vacuum, and the remaining solids are filtered by vacuum on a Whatman #1 filter. The precipitate is washed well with small aliquots of ice-cold acetone, and a sample of the filtrate is analyzed. The precipitate is allowed to dry overnight in vacuo at 20° C., and a sample analyzed.

EXAMPLE 5

Preparative HPLC Purification of α-Cyclodextrin Monotosylate

The following protocol can be used to separate α-cyclodextrin monotosylate from α-cyclodextrin, pyridine and polytosylate. The protocol is for a sample weight of about 80 g and a solvent volume of about 1000 ml.

A hotplate stirrer is used to dissolve the sample in solvent. Filter through a Millipore AP20 or AP25 prefilter. Rewarm and filter through an AP15/0.45 μm HVLP Durapore. Warm flasks in a water batch before loading product onto the HPLC.

The solvent comprises 20 liters of 70:30 vol/vol methanol: water (mix 14 kg Milli-Q Water and a 4.75 kg drum methanol) Vacuum filter through 47 mm 0.45 μm HVLP Durapore. Sparge with Helium for at least six hours.

The following information refers to suggested settings for a Waters Prep LC/System 500. Solvent Flow Rate: 0.35 l/minute; Column: Waters Prep C18 125 Angstroms, 55-104 μm, Cat. No. 25876; Nitrogen Feed Pressure: 490 psi; Pneumatic Drive Pressure: 70 psi; Chamber Pressure: 38 atm; Solvent pressure: 10-12 atm (5-8 for MeOH); Detector Relative Response: 2; Recorder Chart Speed: 5 minutes/cm.

Equilibrate the column with recirculating solvent for 30 minutes. Open the Detector Reference Valve for 3-5 minutes. Close the Reference Valve and set the zero and Off-set controls. Ensure that a 250 ml measuring cylinder of solvent is full. Ensure that a 2.5 l vessel is full of 0.45 μm filtered methanol. Commence loading sample through a solvent inlet. Switch Collect Valve to 5 l vessel after one minute or if baseline starts to change. When the loading of sample is complete, quickly move the inlet tube to the measuring cylinder of solvent (reprime pump if necessary). After 150-200 mls of solvent, switch to the other solvent inlet. Inject 25 μl samples of eluent onto an analytical HPLC at appropriate times. Switch to a 2 l collection vessel when cyclodextrin and residual pyridine have been eluted. If large quantities of pyridine were present it may be necessary to switch to another 2 l vessel before the tosylate elutes. Switch to 20 l collection vessel when tosylate starts to elute. At the end of the tosylate collection, switch the solvent inlet to methanol and also switch the collector to a 2.5 l vessel. Allow at least 1.5 l of methanol the flush to polytosylate from the column. Leave the column filled with methanol.

EXAMPLE 6

Production of 6-Axido-6-Deoxy-α-Cyclodextrin

The materials for this reaction include the α-cyclodextrin monotosylate isolated from the previous Example, sodium axide and TCE, which must be checked for high acidity as previously described.

In 75 ml of distilled water, 683 mg of sodium azide and 683 mg of α-cyclodextrin monotosylate are dissolved. The solution is heated to about 90° C.-95° C. for about 90 minutes and a sample is analyzed. The solution is concentrated in vacuo to approximately 3% of its initial volume, using a controlled vapour temperature of 35° C.–40° C. Higher, temperatures must be avoided to prevent degradation of the product. TCE is added at a ratio of 0.25 ml:2ml of final reaction solution volume. The mixture is agitated vigorously to yield a white precipitate. The precipitate is allowed to settle for one hour and then collected by vacuum filtration using Whatman #1 filter paper. The precipitate is washed on the filter with small aliquots of ice-cold water. Resuspension may, however, provide better results. It is critical that the amount of washing be kept to a minimum because the product can be washed out along with the salts. If further material precipitates out in the filtrate, the filtration is repeated until no more product precipitates. The precipitate is allowed to air-dry. It is noted that the product is not very stable in solution. The precipitate is then suspended in distilled water (50 ml per 75 ml original reaction solution), and the suspension heating in a boiling water bath (or using a heating mantle) until the precipitate dissolves (around 50° C.). The water and TCE are removed by rotary evaporation under vacuum using a water bath temperature of 50° C. This last step may have to be repeated to remove all of the TCE by adding further water and re-evaporating.

EXAMPLE 7

Production of 6-Amino-6-Deoxy-α-Cyclodextrin

To 300 ml of distilled water was added 172 mg of the α-cyclodextrin azide, followed by 30 mg of palladium black. The mixture was shaken or stirred overnight (about 18-24 hours) on a hydrogenator at atmospheric pressure was ambient temperature. It is believed that the reaction was complete after about 20 hours. Samples can be analyzed by TLC to determine when the reaction is complete. About 0.75 ml of TCE are then added, and the mixture is vigorously agitated until an emulsion is obtained. The mixture is then allowed to stand for one hour and then the palladium is filtered off (Whatman #1 followed by 0.45 μm membrane filter). The clear solution is evaporated to dryness (vapour temperature of 45° C.) to yield to crude product amine. This is recrystallized to produce the product amine.

The procedures, equipment and instruments used in Examples 8 to 62 were as follows.

This layer chromatography (t.l.c.) was performed using Kieselgel 60 F$_{254}$ (Merck) on aluminum backing plates. Running solvents used were: solvent A, 14:3:3 butanone-methanol-water; solvent B, 1:8:1 chloroform-acetic acid-water; solvent C, 14:3:3 ethyl acetate-methanol-water. Visualization was achieved by dipping the plate in a solution of either diphenylamine (0.1 g), aniline (0.5 ml) and 85% phosphoric acid (1 ml) in acetone (10 ml), or a solution made up of 10:1 acetone—15% sulfuric acid; and heating to char the spots.

High performance Liquid Chromatography (HPLC) was carried out with a Waters Model 510 Solvent delivery system coupled to a Waters Model 410 differential refractometer. Unless otherwise specified the column used is a Waters 3.9×300 mm Carbohydrate Analysis column ad was run at 1.5 ml.min.$^{-1}$. Infra-red spectra were recorded on a Jasco A102 grating spectrophotometer, a Hitachi 270-30 spectrophotometer or a Perkin-Elmer Model 1720 Fourier Transform spectrophotometer. Samples were prepared as either their Nujol mulls between sodium chloride plates, or as part of the KBr plate. Mass spectra were recorded on a VG ZAB 2HE mass spectrometer using the FAB technique with Xe or Ar as the collision gas. The samples were dissolved in H$_2$O or DMSO and introduced into the spectrometer in a glycerol matrix. A small quantity of trifluoroacetic acid (TFA) was sometimes necessary to produce an adequate spectrum. $^1$H N.m.r. spectra were recorded on a Varian T50 or Bruker CXP300 spectrometer and $^{13}$C n.m.r. were recorded on a Bruker or WP80 spectrometer. Solvents and internal standards are mentioned individually within the text. Melting points were determined using a Reichart melting point apparatus and are uncorrected.

Where multi-O-p-toluenesfulfonyl substituted cyclodextrin derivatives are mentioned in these procedures it should be noted that the exact number and position of substituted hydroxyls is unknown, unless otherwise stated.

Pyridine was dried by storing over freshly activated 4A molecular sieves. p-Toluenesulfonyl chloride was purified according to Vogel, *Textbook of Organic Chemistry*, 4$^{th}$ Ed., p. 317 and stored in a vacuum dessicator over phosphorous pentoxide. α-Cyclodextrin (α-CD) was supplied by Sigma Chemical Co. or Nihon Shokuhin Kako Co. and contained 3% water. β-Cyclodextrin (β-CD) was supplied by Nihon Shokuhin Kako Co. and contained 10% water. β-CD was stored in vacuo over phosphorous pentoxide for at least 48 hours before use. It may also be preferred to dry α-CD before use in the same manner.

EXAMPLE 8

6$^A$-O-p-Toluenesulfonyl-α-cyclodextrin (α-CDOTs)

α-CD (8.0 g) were dissolved in pyridine (800 ml) by gentle warming and shaking. p-Toluenesulfonyl chloride (8.0 g) was added in one portion and the solution stirred at room temperature for 2 hours. The solution was poured onto a mixture of ice cold 6:1 acetone—ether (6 l) and a fine white precipitate formed which was allowed to settle over 1 hour. Most of the supernatent was decanted and the solid collected by gravity filtration (Whatman No 1 filter paper). The filter cake was washed with cold acetone (100 ml in portions) and allowed to air dry overnight to give 6.6 g of crude product. T.l.c. (solvent (A) of the crude product showed: R$_C$(relative to α-CD), α-CD, 1; α-CDOTs, 1.5; α-CD(OTs)$_2$, 1.75. HPLC of the crude product using a 70% CH$_3$CN—H$_2$O eluant showed: t$_R$ (relative to α-CD), α-CD(Ots)$_2$, 0.38; α-CDOTs, 0.52; α-CD, 1.

The crude product (6.6 g) was dissolved in 30% aqueous methanol (100 ml), filtered and loaded via the pump onto a 19×150 mm C$_{18}$ μ-Bondapack HPLC column. This was eluted with 30% aqueous methanol at 15 ml.min$^{-1}$ and gave pure fractions of α-CD (0–35 minutes) and α-CDOTs (1.83 g, 45–120 minutes). This separation procedure is unexpectedly very effective for up to 8 g quantities of the crude product. The column was washed with several column volumes of methanol to elute multi-O-p-toluenesulfonyl substituted cyuclodextrins.

FABMS M+H$^+$ requires 1127, found 1127; M+Na$^+$ requires 1149, found 1149. $^1$H n.m.r. (D$_6$DMSO, CDCl$_3$; TMS standard) δ$_H$ 2.45, CH$_3$; 3.2–5.7, 59H, 7.4–7.8, C$_6$H$_4$. $^{13}$C n.m.r. (D$_6$DMSO) δ$_C$ 25.2$_5$, 64.0$_3$, 73.0$_6$, 73.7$_3$, 75.7$_2$, 76.1$_7$, 77.1$_5$, 77.3$_3$, 85.6$_1$, 86.1$_5$, 105.6$_1$, 106.0$_5$, 131.7$_4$, 134.0$_1$, 136.5$_4$, 148.9$_0$.

EXAMPLE 9

6$^A$-Azido-6$^A$-deoxy-α-cyclodextrin (α-CDN$_5$)

α-CDOTs (540 mg) and sodium azide (540 mg) were dissolved in water (54 ml) and the solution heated on a boiling water bath for 90 minutes. The solution was concentrated in vacuo to approximately 1.5 ml and 1,1,2,2-tetrachloroethane (TCE, 0.25 ml) was added. After vigorous shaking the mixture was left to stand in ice for 10 minutes. The resulting precipitate was collected by centrifugation (3000 rpm, 5 minutes) and washed with ice cold water (2×1.5 ml). The precipitate was resuspended in water (54 ml) and heated on a boiling water bath to release TCE which was removed by pipette. The solution was dried in vacuo to give α-CDNZ$_5$ (410 mg). T.l.c. (solvent A) showed: R$_C$ (relative to α-CD), α-CDN, 0.72. HPLC using a 75% CH$_3$CN—H$_2$O eluant showed: t$_r$ (relative to α-CD), α-CDN$_3$, 0.64.

FABMS M-H$^+$ requires 998, found 998; M+Na$^+$ requires 1020, found 1020. $^{13}$C n.m.r. (D$_6$DMSO, CDCl$_3$, TMS standard) δC 53.0, 60.4$_3$, 70.5$_8$, 72.1$_4$, 72.3$_3$, 72.4$_0$, 82.1$_8$, 83.0$_8$, 102.1$_0$.

EXAMPLE 10

6$^A$-Amino-6$^A$-deoxy-α-cyclodextrin (α-CDNH$_2$)

α-CDN$_3$ (3 g) was dissolved in water (90 ml) and palladium black (90 mg) was added. The mixture was shaken on a Parr hydrogenator under hydrogen (30 psi) at room temperature overnight. After venting the hydrogen, TCE (0.1 ml) was added to the mixture which was then shaken until an emulsion was obtained. After standing for 1 hour the solution was filtered (Whatman N° 1 filter paper) and the clear colorless solution was evaporated to dryness to give α-CDNH$_2$ (2.84 g). T.l.c. (solvent A) showned: R$_C$ (relative to α-CD) α-CDNH$_2$, 0.3. HPLC using a 75% CH$_3$CN—H$_2$O eluant showned: t$_R$ (relative to α-CD), α-CDNH$_2$, 1.2.

FABMS M+H$^+$ requires 972, found 972; M+Na$^+$ requires 994, found 994. $^{13}$C n.m.r. (D$_2$O; dioxane standard δ$_C$42.8$_0$, t, 61.7$_1$, t, 73.2$_1$, d, 73.7$_5$, 74.7$_3$, d, 82.5$_5$, d, 84.3$_7$, d, 102.8$_0$, d.

EXAMPLE 11

$6^A$-O-p-Toulenesulfonyl-$\beta$-cyclodextrin ($\beta$-CDOTs)

$\beta$-CD (13 g) was dissolved in pyridine (100 ml). p-Toluenesculfonyl chloride (1.7 g) was added over a period of 45 minutes with stirring, and the clear solution allowed to stand at room temperature overnight. The pyridine was removed in vacuo and the resulting oily residue triturated with acetone (100 ml). The solid residue was separated by filtration and dissolved in boiling water (50 ml). After cooling, the precipitate was separated by filtration, redissolved in the minimum amount of hot water (50 ml) and filtered hot to remove the less soluble $\beta$-CD(OTs)$_2$. The filtrate was cooled and the solid collected and dried in vacuo over phosphorus pentoxide to give $\beta$-CDOTs (4.5 G). T.l.c. (solvent A) showed: $R_C$ (relative to $\beta$-CD), $\beta$CDOTs, 1.6. HPLC using a 75% CH$_3$CN—H$_2$O eluant showed: $t_R$ (relative to $\beta$-CD, $\beta$-CDOTs, 0.56.

FABMS M+H$^+$ requires 1289, found 1289; M+Na$^+$ requires 1311, found 1311.

EXAMPLE 12

$6^A$-Azido-$6^A$-deoxy-$\beta$-cyclodextrin ($\beta$-CDN$_3$)

$\beta$-CDOTs (2 g) and sodium azide (2 g) were dissolved in water (60 ml) and the solution heated on a boiling water bath for 90 minutes. The solution was concentrated in vacuo to approximately 10 ml. TCE (1 ml) was added and the mixture shaken to a white precipitate. After standing for 60 minutes, the solid was collected by vacuum filtration, washed with small amounts of ice cold water (ca. 3×2 ml) and dried. The collected solid was heated in water (60 ml) until all of the product dissolved. The TCE was removed and the solution evaporated to dryness to give the crude product. T.l.c. (solvent B) showed; $R_C$ (relative to $\beta$-CD), ($\beta$-CDN$_3$), 1.4. HPLC (25 mg in 1 ml H$_2$O) showed; $t_R$ (relative to $\beta$-CD), $\beta$-CDN$_3$, 0.66. Recrystallization from boiling water gives $\beta$-CDN$_3$ as clear colourless crystals.

FABMS M+H$^+$ requires 1160, found 1160; M+Na$^+$ requires 1172, found 1172, $\upsilon_{max}$ 2352 cm$^{-1}$. $^{13}$C n.m.r. (d$_6$DMSO) $\delta_c$ 55.0, 63.9, 74.2, 76.2, 77.0, 85.5, 87.0, 105.9, 106.8.

EXAMPLE 13

Examples 13 to 15 illustrate alternative syntheses for preparing $6^A$-Amino-$6^A$-deoxy-$\beta$-cyclodextrin.

$6^A$-Amino-$6^A$-deoxy-$\beta$-cyclodextrin ($\beta$-CDNH$_2$)

$\beta$-CDN$_3$ (770 mg) was dissolved in water (150 ml) and palladium black (250 mg) was added. The mixture was shaken (18 hours) at 30 psi on a Parr hydrogenator. After venting the hydrogen, a small volume of TCE (1 ml) was added to the mixture which was then shaken for 30 seconds. After standing for 15 minutes the solution was filtered (Whatman N° 1 filter paper) and the clear colourless solution was evaporated to dryness to give $\beta$-CDNH$_2$, (660 mg) T.l.c. (solvent B) showed: $R_C$ (relative to $\beta$-CD), $\beta$-CDNH$_2$, 0.6. HPLC using a 75% CH$_3$CN—H$_2$O eluant snowned: $t_R$ (relative to $\beta$-CD), $\beta$-CDNH$_2$, 1.27.

FABMS M+H$^+$ requires 1134, found 1134. $^{13}$C n.m.r. (D$^6$DMSO) $\delta_C$ 64.1$_5$, t, 72.0$_1$, d, 76.2$_2$, d, 76.5$_5$, d, 77.1$_9$, 85.4$_4$, 85.7$_4$, 85.7$_0$, d 87.7$_0$, d 87.1$_6$, d, 105.4$_9$b, 106.0$^4$, d.

EXAMPLE 14

$\beta$-CDOTs (340 mg) was disclosed in 0.880 ammonia solution (10 ml) and left standing at room temperature for 2 weeks. After removing the ammonia in vacuo the residue was poured into acetone (50 ml). The precipitate was collected by gravity filtration and dried in vacuo to give $\beta$-CDNH$_2$ (301 mg). T.l.c. and HPLC showed only one spot corresponding to $\beta$-CDNH$_2$.

EXAMPLE 15

$\beta$-CDOTs (1 g) was dissolved in DMF (1 ml) and guandine carbonate (1 g) was added. The mixture was heated at 120° C. overnight, then poured into hot ethanol (50 ml). The solvent was decanted and the residue dissolved in hot water and precipitated with ethanol (yield 0.9 g). This solid intermediate was dissolved in KOH solution (2 g in 10 ml water) and heated at reflux overnight. Ammonia is given off. The mixture was poured into ethanol (50 ml) and the product was filtered off, dissolved in water (1 ml) and precipitated with ethanol. The solid was collected to give $\beta$-CDNH$_2$ (0.8 g). T.l.c. showed only one spot corresponding to $\beta$-CDNH$_2$

EXAMPLE 16

$6^A$-Deoxy-$6^A$-iodo-$\beta$-cyclodextrin ($\beta$-CDI)

$\beta$-CDOTs (100 mg) and NaI (100 mg) were heated together in DMF (1 ml) at 80° C. overnight. The solution was poured into acetone (10 ml) and the solid centrifuged down. After recrystallization from water (1 ml) the recovered solid shows only a single spot of t.l.c.: $R_c$ (relative to $\beta$-CD), $\beta$-CDI, 1.57.

EXAMPLE 17

$2^A, 2^B, 2^C, 2^D, 2^E, 2^F, 2^G, 3^A, 3^B, 3^C, 3^D, 3^E, 3^F, 3^G, 6^A, 6^B, 6^C, 6^D, 6^E,$
$6^F$,-Eicosabenzoate-$6^G$-chloro-$\beta$-cyclodextrin
($\beta$-CDClBz$_{20}$)

Dried $\beta$-CDOTs (1 g) was added with stirring to a solution of distilled benzoyl chloride (15.7 g, 13 ml) in dry pyridine (25 ml). The bright pink solution was stirred at 70° C. for 88.5 hours. The brownish colored reaction mixture was concentrated in half volume in vacuo, cooled in ice and cautiously quenched with anhydrous methanol (50 ml). The solution was evaporated to a syrup, diluted with anhydrous methanol (100 ml) followed by water (10 ml) and the solid collected by vacuum filtration. This material was resuspended by dry methanol (100 ml) and stirred for 1 hour before being precipitated with water (10 ml). The white precipitate was collected by vacuum filtration and dried in vacuo to give the product $\beta$-CDClBz$_{20}$ as a powder (2.3 g), T.l.c. (4:1 benzene/ethanol) showed: R$_f$, $\beta$-CDClBz$_{20}$, 0.9.

FABMS M+H$^+$ requires 3233, 3235, found 3233, 3235.

EXAMPLE 18

$2^A$-O-Acetyl-$\alpha$-cyclodextrin ($\alpha$-2CDOAc)

Magnesium turnings (1.2 g) were added to a solution of m-nitrophenol (6.95 g), benzene (40 ml) and acetyl chloride (4 g) and the solution heated for 1 hour at 90° C. The reaction mixture was diluted with ether and decanted from unreacted magnesium. The ether layer was washed successively with water, dilute NaOH and water. The organic layer was dried ($Na_2SO_4$) and the solvent removed in vacuo to give m-nitrophenyl acetate. m.p. 55°–56° C. $^1$H n.m.r. δ2.4, s, 3H, $H_3C$—CO—; 7.4–8.4, m, 4H, ArH. $\nu_{max}$ 1770 cm$^{-1}$.

To a solution of α-CD (0.07 g) dissolved in a pH 9.8 carbonate buffer (62.5 ml) was added 0.2 M m-nitrophenyl acetate in acetonitrile (4.65 ml). After stirring for 13 minutes, diluet HCl was added until the reaction mixture reached pH 4.9. The reaction mixture was cooled to room temperature and any phenol formed extracted with ether. The aqueous layer is concentrated in vacuo to yield a white powder. $^1$H n.m.r. analysis of this powder showed α-2CDOAc to be present in an estimated 5% yield, however total purification could not be achieved due to hydrolysis of the product.

FABMS M+Na$^+$ requires 1038 found 1038. $\nu_{max}$ 1734 cm$^{-1}$.

EXAMPLE 19

6$^4$O-Acetyl-β-cyclodextrin (β-CDOAc)

β-CDOTs (1.3 g) and cesium acetate (0.6 g) were dissolved in DMF (10 ml) and stirred at 110°–120° for 20 hours. After cooling the reaction mixture, excess acetone was added until precipitation was complete and the product was collected by vacuum filtration (yield 1.0 g). Recrystallization from water followed by Sephadex G15 chromatography (5:1 acetontile : water) of the crude product gave β-CDOAc (0.4 g). FABMS M+H$^+$ requires 1177, found 1177. $\nu_{max}$ 1736 cm$^{-1}$.

EXAMPLE 20

6$^4$-Acetamido-6$^4$-deoxy-α-cyclodextrin (α-CDNAc)

To a solution of α-CDNH$_2$ (100 mg) dissolved in dry methanol (7.5 ml), was added acetic anhydride (1.5 ml) and the reaction mixture stirred for 6 hours. Water (1.5 ml) was added followed by acetone (20 ml) to precipitate the product. The precipitate was separated by filtration through fluted N° 50 qualitative Whatman filter paper and washed with acetone to give crude product (146 mg). T.l.c. (solvent A) of the crude product showed: R$_c$ (relative to α-CD), α-CDNH$_2$0.7; α-CDNAc, 1.1. HPLC of the crude product using a 75% CH$_3$CN—H$_2$O eluant showed: t$_R$ (relative to α-CD), unknown, 0.6; α-CDNHAc, 0.9; α-CDNH$_2$, 1.2.

α-CDNAc was separated by preparative HPLC. FABMS M+H$^+$ requires 1014, found 1014;1 M+NA$^+$ requires 1036, found 1036.

EXAMPLE 21

Examples 21 to 25 illustrate preparation of prodrugs in which Ibuprofen or Naproxen are covalently bonded directly to a cyclodextrin through ester linkages.

2$^4$-O-(α-Methyl-4-isobutylphenylacetyl)-α-cyclodextri (α-2CDOIb)

Step 1: The m-nitrophenyl ester of Ibuprofen (m-NO2PhOIb) can be prepared as follows. Ibuprofan (1.03 g) and m-nitrophenol (0.7 g) were dissolved in dry ethyl acetate (100 ml). The mixture was cooled to 0° C. and dicyclohexylcarbodiimide (DCC) (1.68 g) was added. After being left at 0° C. for 1 hours, the reaction mixture was warmed to room temperature and left stirring overnight. Dicyclohexylurea (DCU) was removed by filtration through Whatman N° 1 filter paper. Evaporation of the filtrate in vacuo yielded the crude ester as a glassy thick liquid (1.27 g). T.l.c. (petroleum ether showed: R$_f$, m-nitrophenyl, 0.2; Unknown, 0.35; m-NO2PhOIb, 0.5. The ester was purified using flash chromatography (Matrex Silica Gel, 50 μm) and 0% to 100% ethyl acetate-petroleum ether as eluants. $\nu_{max}$ 1760 cm$^{-1}$ (C=O). $^1$H n.m.r. (CDCl$_3$; TMS standard) δH 1.0, d, (J 6 Hz), 6H, (CH$_3$)$_2$CH—; 1.66, d, (J, 7 Hz), 3H, —CH$_3$; 2.5, d, (J, 7 Hz), 2H, —CH$_2$—, 4.0, q, (J, 7 Hz), 1H, H$_3$C—CH, 7.0–7.8, m, 4H, ArH.

Step 2: α-CD (0.97 g) was dissolved in a 1:1 mixture of aqueous NaOH (4×10$^{-3}$ M)—acetonitrile (80 ml). The m-nitrophenyl ester of Ibuprofen (0.33 g) in acetonitrile (10 ml) was added gradually with stirring, and NaOH (0.1 M) was added until the reactio mixture reached pH 10. After being left to stir for 100 minutes, hydrochloric acid (4 N) was added to the reaction mixture until it reached pH 2.5. Chloroform (50 ml) was added to the reaction mixture and the organic layer was separated, dried (Na$_2$SO$_4$) and the solvent removed in vacuo. Ether was used to dissolved the soluble m-nitrophenyl, leaving behind the crude product (0.2 g).

Preparative HPLC enabled the separation of α-2CDOIb. FABMS M+H$^+$ requires 1161 found 1161; M+N$^+$ requires 1183, found 1183. $\nu_{max}$ 1728 cm$^{-1}$ (C=O).

EXAMPLE 22

2$^4$-O-(α-Methyl-4-isobutylphenylacetyl)-β-cyclodextrin (β-2CDOIb)

β-CD (1-mmol) was dissolved in a 1:1 mixture of aqueous NaOH (5×10$^{-4}$ M)—acetonitrile (10 ml). The m-nitrophenyl ester of Ibuprofen (Example 21, Step 1; 0.327 g) in acetonitrile (10 ml) was gradually added with stirring and NaOH (0.1 M) was added until the reaction mixture reached pH 10. After being left to stir at room temperature for one hour, hydrochloric acid (3 M) was added to the reaction mixture until it reached pH 2.5. Water was removed by distillation at 40° C. under reduced pressure. The solid was redissolved in water and filtered, and the filtrate extracted with ether to remove m-nitrophenyl. The water was removed by distillation under reduced pressure to give a solid. HPLC of this solid using a 70% CH$_2$CN—H$_2$O showed: t$_R$ (relative to β-CD), β-2CDOIb, 0.65.

FABMS M+H$^+$ requires 1323, found 1323. $\nu_{max}$ 1728 cm$^{-1}$.

EXAMPLE 23

6$^4$-O-(α-Methyl-4-isobutylphenylacetyl)-α-cyclodextrin (α-CDOIb)

α-CDTs (1 g) and the potassium salt of Ibuprofan (600 mg) were heated in DMF (5 ml) at 100° C. for 24 hours. The reaction mixture was cooled and acetone was added until precipitation was complete. The mixture was filtered and the solid was washed with acetone and collected. The product mixture was chromatographed on Sephadex G15 and the major product (α-CDOIb) was isolated together with a small amount of α-CD (yield 0.7 g). FABMS M+Na$^+$ requires 1183, found 1183. M+K$^+$ requires 1200, found 1200.

The reaction was repeated using sodium and cesium salts of Ibuprofen to give the same product mixture.

EXAMPLE 24

6$^4$-O-(α-Methyl-4-isobutylphenylacetyl)-β-cyclodextrin (β-CDOIb)

Step 1: β-CDOTs (200 mg) and the sodium salt of Ibuprofen (60 mg) were stirred and heated in DMF (2 ml) at 100° C. for 20 hours. The reaction mixture was cooled and acetone added until precipitation was complete. The mixture was filtered and the solid was washed with acetone and recrystallized from water to give crude product. HPLC of the crude product using a 70% CH$_3$CN—H$_2$O eluant showed: $t_R$ (relative to β-CD), 0.32, 0.38. A portion of the crude product was separated by preparative HPLC to separate two solids, identified by FABMS and $^1$H n.m.r. as isomers of β-CDOIb. FABMS M+H$^+$ requires 1323, found 1323; M+Na$^+$ requires 134,5 found 1345, $v_{max}$ 1735 cm$^{-1}$.

The reaction was repeated using potassium and cesium salts of Ibuprofen to give the same isomeric mixture.

Step 2: Separation of the mixture of isomers of 6$^A$-O-(α-methyl-4-isobutylphenylacetyl)-β-cyclodextrin was achieved as follows. βCDOIb (a mixture of isomers from Example 27, 215 mg), imidazole (617 mg) and dimethylaminopyridine (2.2 mg) where dissolved in dry DMF (10 ml). Under nitrogen, thexyldimethyl-silyl-chloride (1ml) was added through a syringe and the mixture heated to 100° C. and stirred overnight. The solvent was removed and the product was chromatographed on silica gel using petroleum ether—chloroform as eluants. The separated components were treated with tetrabutylammoniumfluouride to give the individual isomers of βCDOIb.

EXAMPLE 25

6$^A$-O-((+)-α-Methyl-6-methoxy-2-napthylacetyl)-β-cyclodextrin (β-CDONp)

To a solution of β-CDOTS (2.5 g) in dry DMF (30 ml) was added to the cesium salt of Naproxen (0.8 g). The mixture was stirred for 18 hours at 100°-110° C., cooled and acetone added until precipitation was complete. The precipitate (2 g) was collected by gravity filtration (Whatman N° 1 qualitative filter paper) and rerystallization from water. HPLC using 70% CH$_3$CH—H$_2$O as eluant showed: $t_R$ (Relative to β-CD), β-CDONp, 0.28.

FABMS M+H$^+$ requires 1347, found 1347. $v_{max}$ 1736 cm$^{-1}$.

EXAMPLE 26

Example 26-31 illustrate preparation of prodrugs in which Ibuprofen or Naproxen is covalently bonded directly to a cyclodextri through amide linkages.

6$^A$-Deoxy-6$^A$-(α-methyl-4-isobutylphenylacetamido)-α-cyclodextrin (α-CDNIb)

Step 1: The symmetric anhydride of Ibuprofen (Ib$_2$O) was prepared as follows. Ibuprofen (1500 mg) was dissolved in dry ether (60 ml) and DCC (750 mg) was added. Insoluble DCU forms immediately. After 1 hour the ether was removed in vacuo and ethyl acetate (600 ml) was added to the residue. The product only slowly dissolved in ethyl acetate so sufficient agitation and time was required to ensure solubilization. The insoluble DCU was filtered off and ethyl acetate removed in vacuo to give Ib$_2$O.

Step 2: α-CDNH$_2$ (600 mg) was dissolved in dry methanol (13 ml) and the Ib$_2$O (1.3 g) added. The reaction was stirred at room temperature for 6 hours and water (20 ml) added. The mixture was stirred for a further 10 minutes and then filtered (Whatman N° 1 further paper) directly into acetone (200 ml). The resulting precipitate was collected by gravity filtration and washed with acetone (2×20 ml). The resultant solid was dried in vacuo to give both α-CDNIb and α-CDNH$_2$ (370 g).

A portion of this material was passed through an Amberlite CG-120 (Type, 1, 100–200 mesh) BDH ion exchange column, in its protonated form an remove α-CDNH$_2$ which was recovered by further elution with 4% ammonia solution.

$^1$H n.m.r. and $^{13}$C n.m.r. indicate an isomeric mixture of the Ibuprofen derivative. $^1$H n.m.r. (D$_2$O, Dioxane standard) δH 0.87, J 7 Hz Me$_{iBu}$, Me$_{iBu}$; 1.34, J 7 Hz, 1.39, J 7 Hz, αMe (2 isomers); 1.84, m, J 7 Hz, CH$_{iBu}$; 2.48, J. 7 Hz, (CH$_2$) iBu; 3.2–5.1, 60 H 7.23, q, ArH. $^{13}$C n.m.r. (D$_2$O, dioxane standard) δc 18.5$_0$, q, 18.9$_5$, q, 23.3$_0$, q, 30.9$_2$, d, 41.2$_4$, t, 41.5$_3$, t, 45.7$_8$, t, 46.7$_1$, d, 47.1$_6$, d, 61.5$_9$, t, 71.7$_4$, 72.9$_2$, d, 73.2$_8$, d, 74.6$_5$, d, 82.2$_0$, d, 82.5$_0$, d, 84.0$_2$, 84.4$_0$, 102.7$_0$, d, 126.6$_5$, s, 128.2$_8$, d, 128.4$_9$, d, 130.6$_8$, d, 139.7$_5$, s, 140.0$_0$, s, 142.2$_1$, s.

EXAMPLE 27

To a solution of α-CDNH$_2$ (10 mg) in dry DMF (0.2 ml) was added a solution of the m-nitrophenyl ester of Ibuprofen (Example 21, Step 1; 5 mg) in dry DMF (0.2 ml) and the reaction mixture stirred at 80° C. for 24 hours. Water was added and then acetone to precipitate the product. The precipitate was separated by filtration through fluted N° 50 qualitative Whatman filter paper, washed with acetone and the solid collected and dried in vacuo to give a material with the same HPLC characteristics as α-CDNIb.

EXAMPLE 28

To a solution of Ibuprofen (8.5 mg), ethyl chloroformate (4.5 mg) and triethylamine (4.2 mg) in DMF (0.5 ml) was added α-CDNH$_2$ (10 mg) and the reaction mixture stirred at 80° C. for 24 hours. Water was added followed by acetone to precipitate the product. The precipitate was separated by filtration through fluted N° 50 qualitative Whatman filter paper, washed with acetone and the solid collected and dried in vacuo to give a material with the same HPLC characteristics as α-CDNIb.

EXAMPLE 29

$^A$-Deoxy-6$^A$-(α-methyl-4-isobutylphenylacetamdo)-β-cyclodextrin (β-CDNIb)

A mixture of β-CDNH$_2$ (845 mg) and Ib$_2$O (Example 26, Step 1; 1700 mg) were dissolved in methanol (20 ml) and refluxed overnight. After cooling, the mixture was poured into acetone (100 ml). The resulting precipitate was collected by gravity filtration (Whatman N° 1 filter paper), washed with acetone and recrystallized from water to give β-CDNIb (522 mg). m.p. 271°–274° C. T.l.c. (solvent B) showed: R$_c$ (Relative to β-CD), β-CDNIb, 1.3. HPLC using 70% CH$_3$CN—H$_2$O as eluant showed: $t_R$ (Relative to β-CD), β-CDNHIb, 0.27.

FABMS M+H$^+$ requires 1322 found 1322; M+Na$^+$ requires 1344 found 1344. $v_{max}$ (KBr) 1651 cm$^{-1}$.

EXAMPLE 39

6$^A$-Deoxy-6$^A$((+)-α-methyl-6-methoxy-2-naphthylacetamido)-α-cyclodextrin (α-CDNNp)

Step 1: The anhydride of Naproxen (Np$_2$O) was prepared as follows. Naproxen (250 mg) was dissolved in dry ether (10 ml) and DCC (130 mg) was added. Insoluble DCU forms immediately. After 1 hour the ether was removed in vacuo and ethyl acetate (100 ml) added to the residue. The product only slowly dissolved in ethyl acetate so sufficient agitation and time was required to ensure solubilization. The insoluble DCU was filtered off and ethyl acetate removed in vacuo to yield Np$_2$O.

Step 2: α-CDNH$_2$ (28 mg) was dissolved in dry methanol (0.65 ml) and the Np$_2$O (60 mg) added. The reaction was stirred at room temperature overnight. Acetone was added until precipitation appeared complete. The resulting precipitate was collected by gravity filtration (Whatman N° 1 filter paper) and washed with acetone. The solid was collected and dried in vacuo. HPLC analysis showed two major and two minor products. FABMS (crude) M+H$^+$ requires 1184, found 1184; M+Na$^+$ requires 1206, found 1206.

EXAMPLE 31

6$^A$-Deoxy-6$^A$-((+)-α-methyl-6-methoxy-2-naphthylacetamido) -β-cyclodextrin (β-CDNNp)

βCDNH$_2$ (800 mg) and Np$_2$O (Example 30, Step 1; 1600 mg) were dissolved in a mixture of methanol and DMF (3:1; 16 ml) and refluxed overnight. The methanol was then removed in vacuo and the residue poured into acetone (60 ml). The resulting precipitate was collected by gravity filtration (Whatman N° 1 filter paper), washed with acetone and recrystallized from water to give β-CDNNp (525 mg). T.l.c. (solvent B) showed; R$_C$ (Relative to β-CD), β-CDNNp, 1.5. HPLC using 70% CH$_3$CN—H$_2$O as eluant showed: t$_R$ (Relative to β-CD), β-CDNNp, 0.35.

m.p. 295°–297° C. FABMS M+H$^+$ requires 1346 found 1346. ν$_{max}$ 1608, 1629 cm$^{-1}$.

6$^A$-Deoxy-6$^A$-(aminoalkylamino)-cyclodextrins

The preparation of 6$^A$-deoxy-6$^A$-(4-aminobutylamino)-a-cyclodextrin described in Example 32 is representative of the procedures used in Example 32 to 39.

EXAMPLE 32

6$^A$-Deoxy-6$^A$-(4-aminobutylamino)-α-cyclodextrin (α-CDN4N)

α-CDOTS (86 mg) and 1,4-diaminobutane (0.3 ml) were heated together at 70° C. for 3 hours. T.l.c. (solvent A) indicated that there was no α-CDOTs left. Acetone (4 ml) was added and the resulting suspension centrifuged. Following removal of the supernatent, the solid was dissolved in water (0.1 ml), precipitated with acetone (4 ml) and centrifuged. The solid was collected and dried in a vacuum desiccator over phosphorus pentoxide, to yield an off-white powder (84 mg) which still smelt of diaminobutane. The crude product was dissolved in boiling water (1.0 ml) and filtered hot. Ethanol was added to the boiling solution until turbidity was retained, followed by the addition of water until the solution remained clear. Upon cooling, pure α-CDN4N crystals formed, which were collected by gravity filtration (Whatman N° 1 filter paper) and washed (1:1 ethanol/water, 1 ml).

FABMS M+H$^+$ requires 1043, found 1043. $^1$H n.m.r. (D$_6$DMSO) δ$_H$ 1.3–3.0, 10H; 3.1–4.9, 60H. $^{13}$C n.m.r. (D$_6$DMSO) δ$_C$ 30.8$_9$, 33.11$_2$, 44.5$_6$, 53.2$_3$, 64.2$_0$, 74.7$_4$, 76.2$_4$, 77.4$_0$, 86.2$_1$, 87.9$_8$, 106.0$_6$.

EXAMPLE 33

6$^A$-Deoxy-6$^A$-(2-aminoethylamino)-α-cyclodextrin (α-CDN2N)

FABMS M+H$^+$ requires 1015, found 1015.

EXAMPLE 34

6$^A$-Deoxy-6$^A$-(3-amiopropylamino)-α-cyclodextrin (α-CDN3N)

FABMS M+H$^+$ requires 1029, found 1029.

EXAMPLE 35

6$^A$-Deoxy-6$^A$-(6-aminohexylamino)-α-cyclodextrin (α-CND6N)

FABMS M+H$^+$ requires 1071 fond 1071. $^1$H n.m.r. (D$_6$ DMSO) δ$_H$ 1.2–3.1, 14H; 3.3–5.5, 60H. $^{13}$C n.m.r. (D$_6$ DMSO) δ$_C$ 30.1$_3$, 30.5$_1$, 33.2$_3$, 35.3$_1$, 44.6$_7$, 53.5$_1$, 60.0$_7$, 64.0$_7$74.7$_5$, 76.1$_7$, 77.3$_1$, 86.1$_6$, 87.8$_7$, 105.9$_7$.

EXAMPLE 36

6$^A$-Deoxy-6$^A$-(2-aminoethylamino)-β-cyclodextrin (β-CDN2N)

Ion-exchange chromatography on cellulose-based or resin-based cation exchange columns were used to obtain β-CDN2N free of β-CD.

FABMS M+H$^+$ requires 1177, found 1177. $^1$H n.m.r. (D$_6$DMSO) δ$_H$ 2.4–3.0, 6H; 3.2–5.5, 70H, $^{13}$C.n.m.r. (D$_6$DMSO) δ$_C$ 44.9$_8$, 53.3$_9$, 55.1$_6$, 64.1$_6$, 74.5$_6$, 76.2$_6$, 76.5$_7$, 77.2$_8$, 85.7$_5$, 87.6$_5$, 106.1$_4$.

EXAMPLE 37

6$^A$-Deoxy-6$^A$-(3-aminopropylamino)-β-cyclodextrin (β-CDN3N)

FABMS M+H$^+$ requires 1191, found 1191.

EXAMPLE 38

6$^A$-Deoxy-6$^A$-(4-aminobutylamino)-β-cyclodextrin (β-CDN4N)

Precipitation was effected by the addition of ethanol rather than acetone. The solid was filtered off and recrystallized twice by dissolving in hot water/ethanol (2:1) then filtering, and adding hot ethanol and cooling. The solid contains very large quantities of solvent, and loses up to 40% of it's weight upon drying.

M.p. 285° C. FABMS M+H$^+$ requires 1205, found 1205. $^{13}$C n.m.r. (D$_2$O; dioxane standard) δ$_C$27.1$_7$, 29.3$_4$, 30.0$_8$, 41.2$_8$, 41.4$_7$, 49.4$_3$, 50.3$_3$, 58.5$_5$, 71.0$_4$, 73.2$_4$, 74.4$_5$, 83.0$_4$, 82.3$_6$, 85.0$_8$, 102.9$_4$, 103.2

EXAMPLE 39

6$^A$-Deoxy-6$^A$-(6-aminohexylamino)-β-cyclodextrin (β-CDN6N)

The crude solid did not recrystalline from ethanol/water. Purification was achieved by precipitation of an aqueous solution with acetone (twice).

FABMS M+H$^+$ requires 1233, found 1233. $^1$H n.m.r. (D$_6$DMSO) δ$_H$ 1.2–3.0, 14H; 3.1–6.0, 70H. $^{13}$C n.m.r. (D$_2$O: dioxane std) δ$_C$ 26.7$_9$, 27.1$_7$, 28.6$_5$, 30.6$_0$, 41.3$_4$, 48.3$_2$, 48.3$_2$, 49.4$_5$, 61.2, 70.1$_9$, 73.1$_6$, 74.3$_8$, 81.2$_6$, 82.2$_8$, 84.0$_6$, 101.9$_1$, 103.0.

EXAMPLE 40

6$^A$-Deoxy-6$^A$-(1,4-diazacyclohexyl)-β-cyclodextrin (β-CDN2,2N)

β-CDOTs (1g) and piperazine hexahydrate (2 g) were heated together in DMF (1 ml) at 70° C. for 14 hours. The mixture was poured into ethanol (50 ml) and stirred for one hour. The solid was filtered off and recrystallized from water/ethanol (50 ml), yielding 800 mg of a white crystalline solid after drying in vacuo.

FABMS M+H+ requires 1203, found 1203.

EXAMPLE 41

6$^A$-Deoxy-6$^A$-(4-aminophenylamino)-β-cyclodextrin (β-CDNPhN)

β-DCOTs (100 mg) and 1,4-diaminobenzene (100 mg) were heated together in DMF (1 ml) at 80° C. overnight. The black fluid was poured into acetone (10 ml) and the solid separated by centrifugation. The solid was dissolved in water (1 ml) and precipitated by pouring into ethanol (10 ml), and then centrifuged, washed with ethanol (1 ml) and dried in vacuo.

FABMS M+H+ found 1225, required 1225.

EXAMPLE 42

6$^A$-Deoxy-6$^A$-(4-aminophenylamino)-α-cyclodextrin (α-CDNPhN)

α-CDOTs (100 mg) and 1,4-diaminobenzene (100 mg) were heated together in DMF (1 ml) at 80° C. overnight. The black fluid was poured into acetone (10 ml) and the solid separated by centrifugation. The solid was dissolved in water (1 ml) and precipitated by pouring into ethanol (10 ml), and then centrifuged, washed with ethanol (1 ml) and dried in vacuo.

EXAMPLE 43

6$^A$-Deoxy-6$^A$-(2,2-diethoxyethylamino)-β-cyclodextrin (β-CDN2 1 Oet)$_2$)

The diethylacetal of 2-amino-ethanol (3 ml) and β-CDOTs (1 g) were dissolved in pyridine (1 ml) and the mixture was left at 80° C. for 3 hours. The product was precipitated in acetone.

FABMS M+H+ requires 1250, found 1250.

EXAMPLE 44

6$^A$-Deoxy-6$^A$-(1-carboxypropylamino)-β-cyclodextrin (β-CDN2CO$_2$)

Reaction of β-CDOTs (1 g) with 4-aminobutanoic acid in pyridine/DMF (1:1, 1 ml) proceeded rapidly. Separation of product from excess amine was achieved by repeated precipitation in ethanol.

EXAMPLE 45

6$^A$-Deoxy-6$^A$-(1-carboxyethylamino)-β-cyclodextrin (β-CDN2CO$_2$)

Reaction of β-CDOTs (1 g) with β-alanine in pyridine/DMF (1:1, 1 ml) proceeded rapidly. Separation of product was achieved by precipitation in ethanol.

EXAMPLE 46

Examples 50 to 56 exemplify the production of a prodrug in which Ibuprofen is covalently bonded to a cyclodextrin via an amide linking group formed on a pendant arm.

6$^A$-Deoxy-6$^A$-(4-(α-methyl-4-isobutylphenylacetamido)-butylamino) β-cyclodextrin (β0CDN4NIb)

Step 1: The acid chloride of Ibuprofen (IbCl) is prepared as follows. Ibuprofen (4 g), was heated in thionyl chloride (10 ml) at 70° C. for 4 hours and the solvent was removed in vacuo at 70° C. The residue is a colourless oil. Infra red shows no OH.

Step 2: Vacuum dried β-CDN4N (1 g) was dissolved in DMF (3 ml) and IbCl (300 mg) was added, and the reaction mixture left overnight. The reaction mixture was poured into acetone (50 ml) and the precipitate was collected by centrifugation and recrystallization from 50% ethanol. T.l.c. indicates the product is a mixture of 3 components one being β-CDN4NIb.

EXAMPLE 47

β-CDN4N (51 mg) was dissolved in dry DMF (1 ml) and Ib$_2$O (Example 26, Step 1: 100 mg) added. The solution was left overnight at room temperature and acetone (10 ml) was added to form a precipitate. The resulting mixture was centrifuged and the supernatant discarded. The solid was recrystallized from ethanol/water (1:1, 2 ml). The collected crystals were dried in vacuo over phosphorus pentoxide. (Yield 36 mg)

The mixture of amides slowly hydrolyses on storage in the dark at room temperature.

EXAMPLE 48

Step 1: 4-(α-Methyl-4-isobutylphenylacetamido)-butylamine is prepared as follows. 1,4-Diaminobutane (10 g) was dissolved in dichloromethane (50 ml). The solution was stirred vigorously and IbCl (Example 46, Step 1; 1 g) was added dropwise. The reaction mixture was allowed to stand for 4 hours and ether (100 ml) added. The mixture was washed with dilute sodium bicarbonate solution and twice with water (40 ml), dried with sodium sulfate and the solvent removed. The residue was recrystallized twice from chloroform-petroleum ether to give the product (800 mg) as off-white crystals.

Step 2: β-CDOTs (1 g) and 4-(α-methyl-4-isobutylphenyl-acetamido) -butylamine (1 g) were dissolved in DMF (1 ml) and pyridine (0.5 ml) and heated at 70° C. overnight. The product was purified by precipitation in acetone and recrystallization from ethanol/water. HPLC showed: t$_R$ (Relative to βCD), 0.26.

EXAMPLE 49

6$^A$-Deoxy-6$^A$-(4-(α-methyl-4-isobutyl-phenylacetamido)-butylamino) -α-cyclodextrin (α-CDN4NIb)

α-CDN4N was reacted with Ib$_2$O (Example 26, Step 1; 2 equivalents) in DMF at room temperature. The mixture was poured into acetone and the resultant precipitate separated by centrifugation. This solid was recrystallized from 1:1 EtOH/water.

FABMS M+H+ requires 1232 found 1232.

EXAMPLE 50

6$^A$-Deoxy-6$^A$-(4-(α-methyl-4-isobutylphenylacyl)-1,4-diazacyclohexyl)-β-cylodextrin (β-CDN2, 2NIb)

β-CDN2, 2N (0.5 g) was dissolved in DMF (1.5 ml) and IbCl (Example 46, Step 1; 160 mg) was added. The reaction mixture was left overnight and then poured into acetone (50 ml). The precipitate was collected by centrifugation and recrystallization from 50% aqueous ethanol. T.l.c. indicated the product is a mixture of 3 components, one being β-CDN2,2NIb.

EXAMPLE 51

Preparation of disulfide linked β-cyclodextrin (β-CD$_2$S$_2$)

βCDOTs (2 g) and thiourea (2 g) were refluxed for 48 hours in 80% aqueous methanol (100 ml). The solvent was removed by distillation under reduced pressure to give a white solid. Methanol (30 ml) was added and the mixture stirred for 1 hour. The solid was filtered (1.5 g crude yield) and 70 ml of a 10% sodium hydroxide solution was added. The solution was heated at 70° C. for 7 hours. After cooling, the pH of the solution was adjusted to pH 2 by the addition of 10% hydrochloric acid. Trichloroethylene (10 ml) was added, and the mixture was stirred overnight. The precipitate was filtered, washed with water, and repeatedly recrystallized from water (Yield 1 g)

FABMS $\beta$CDSH+H$^+$ requires 1151, found 1151, $\beta$CD—S—C (NH$_2$)+H$^+$ requires 1193, found 1193; $\beta$CD+H$^+$+CClHCCl$_2$ requires 1266, found 1266; $\beta$CDSH+H$^+$+CClHCCl$_2$ requires 1282, found 1282; $\beta$-CD$_2$S$_2$+H$^+$ requires 2300 found 2300.

This solid was allowed to oxidize in air for a longer time to increase the yield of the dimer.

EXAMPLE 52

N,N'-bis-(6$^4$-deoxy-6$^4$-$\alpha$-cyclodextrin)-succinamide ($\alpha$-CD$_2$NSuc)

Step 1: Preparation of bis-(3-nitrophenyl) succinate. Succinic acid (1.8 g) and m-nitrophenol (2 mole equiv) were dissolved in ethyl acetate (100 ml). While stirring in an ice bath, DCC (4 g) were added and the mixture stirred at 0° C. for 1 hour and then at room temperature overnight. The ester was purified by silica gel chromatography $\nu_{max}$ 1750 cm$^{-1}$.

Step 2: $\alpha$-CDNH$_2$ (100 mg) was dissolved in DMF (4 ml), and bis-(3-nitrophenyl) succinate (20 mg) was added in one portion and the mixture stirred 18 hours at room temperature. Acetone (50 ml) was added and the white precipitate gravity filtered through Whatman N° 52 filter paper. The solid was washed with acetone (yield 80 mg). T.l.c. and HPLC of the crude product showed a mixture of products.

These were partially separated by preparative HPLC to enable identification of an amide-ester succinate capped $\alpha$-cyclodextrin (FABMS capped-CD+H$^+$ requires 1054, found 1054) and N,N'-bis-(6$^4$-deoxy-6$^4$-$\alpha$-cyclodextrin)-succinamide (FABMS M'H$^+$ requires 2026, found 2026).

EXAMPLE 53

Bis-(2$^4$-deoxy-2$^4$-$\beta$-cyclodextrin) succinate (2$\beta$-CD$_2$OSuc)

$\beta$CD (1.1 g) was dissolved in water (50 ml) and bis-(3-nitrophenyl) succinate (Example 52, Step 1; 0.15 g) in acetonitrile (10 ml) added in one portion. The reaction mixture turned yellow. After stirring for 5 minutes, dilute hydrochloric acid was added to the reaction mixture until if reached pH 3. The solution was cooled and filtered to remove any unreacted $\beta$-CD. The filtrate was extracted twice with ether and the aqueous solvent removed in vacuo. T.l.c. analysis of the residue showed the main component to be $\beta$-CD which was the only compound to be isolated by chromatography.

EXAMPLE 54

N,N'-bis-I(6$^4$-deoxy-6$^4$-$\beta$-cyclodextrin)-succinamide ($\beta$-CD$_2$NSuc)

To a solution of $\beta$-CDNH$_2$ (120 g) in DMF (10 ml) was added bis-(3-nitrophenyl) succinate (Example 52, Step 1; 20 mg) in small portions over 6 days, at the end of which t.l.c. showed only 1 spot. The solvent was removed in vacuo (oil pump) to give an oil which was triturated with acetone (50 ml) to give an off-which solid. The solid was collected by filtration and washed with acetone (2×10 ml), then with ether (2×10 ml), and dried in vacuo to give 90 mg of crude product. HPLC of the crude mixture showed a mixture of compounds, one of which was $\beta$-CD$_2$NSuc.

FABMS M+H$^+$ requires 2350, found 2350.

EXAMPLE 55

6$^4$-Acrylamido-6A-deoxy-$\beta$-cyclodextrin ($\beta$-CDNCO=C)

To a solution of $\beta$-CDNH$_2$ (25 mg) and sodium hydroxide (1.7 mg) in water (2 ml) was added acryloyl chloride (4.5 ml) with vigorous stirring at 0° C. T.l.c. (solvent A) showed: R$_C$ (relative to $\beta$-CD), $\beta$-CDNCO=C, 1.4. Acetone was added and the precipitate collected by centrifugation and decantation to give a solid. FABMS M+H$^+$ requires 1188, found 1188; M+Na$^+$ requires 1210 found 1210.

It will be apparent to those skilled in the art that various modifications and variations can be made to the compositions of matter and methods of this invention. Thus, it is intended that the present invention cover the modifications and variations of this invention provided they come within the scope of the appended claims and their equivalents. All references in the claims to a composition of matter such as an inclusion complex, cyclodextrin derivative, intermediate, linked cyclodextrins, prodrug, composition, a process reactant, and pharmaceutical, pesticidal, herbicidal, agricultural, cosmetic or personal care agent, whether in general or by name, expressly includes the salts and hydrates thereof.

What is claimed is:

1. A process for isolating a cyclodextrin or derivative thereof from a solution that contains said cyclodextrin or derivative thereof and a powder catalyst, said process comprising the steps of:
   A. adding a small volume of coagulating agent to the said solution to effect coagulation of the powder catalyst; and
   B. separating the coagulated powder from the solution.

2. A process according to claim 1, wherein the coagulating agent is 1,1,2,2-tetrachloroethane.

3. A process according to claim 1, wherein the catalyst powder is selected from powder comprising palladium, platinum or nickel.

4. A process according to claim 1, wherein the cyclodextrin derivative is 6$^4$-amino-6$^4$-deoxy-cyclodextrin.

5. A process according to claim 4, wherein the cyclodextrin derivative is 6$^4$-amino-6$^4$-deoxy-$\alpha$-cyclodextrin.

6. A process according to claim 4, wherein the cyclodextrin derivative is 6$^4$-amino-6$^4$-deoxy-$\beta$-cyclodextrin.

7. A process according to claim 4, wherein the cyclodextrin derivative is 6$^4$-amino-6$^4$-deoxy-$\gamma$-cyclodextrin.

* * * * *